United States Patent [19]

Rock

[11] Patent Number: 5,928,647
[45] Date of Patent: *Jul. 27, 1999

[54] INDUCING CYTOTOXIC T LYMPHOCYTE RESPONSES

[75] Inventor: Kenneth Rock, Chestnut Hill, Mass.

[73] Assignee: Dana-Farber Cancer Institute, Boston, Mass.

[*] Notice: This patent is subject to a terminal disclaimer.

[21] Appl. No.: 08/481,327

[22] PCT Filed: Jan. 10, 1994

[86] PCT No.: PCT/US94/00362

§ 371 Date: Sep. 15, 1995

§ 102(e) Date: Sep. 15, 1995

[87] PCT Pub. No.: WO94/15635

PCT Pub. Date: Jul. 21, 1994

Related U.S. Application Data

[63] Continuation-in-part of application No. 08/003,233, Jan. 11, 1993, abandoned.

[51] Int. Cl.$^6$ .................................................. A61K 39/385
[52] U.S. Cl. ................................ 424/196.11; 424/197.11; 424/204.1; 424/234.1; 424/491
[58] Field of Search .......................... 424/278.1, 280.1, 424/277.1, 204.1, 234.1, 486, 490, 491, 496, 497, 196.11, 197.11; 514/951

[56] References Cited

U.S. PATENT DOCUMENTS 5,045,320   9/1991   Mescher .................................. 436/527

OTHER PUBLICATIONS

Remington's Pharmaceutical Sciences, 18$^{th}$ GD., p. 1280.

*Primary Examiner*—Donna C. Wortman
*Attorney, Agent, or Firm*—Seed and Berry LLP

[57] ABSTRACT

The invention provides compositions and methods for inducing MHC class I-restricted cytotoxic T lymphocyte responses in a mammalian host by immunization with non-replicating protein antigens. The compositions of the invention comprise a particulate-protein complex capable of inducing a class I-restricted CTL response to a protein antigen in a mammal, in which the particulate protein complex comprises a particulate component having an average diameter ranging in size from about 0.5 $\mu$m to about 6 $\mu$m, linked to a non-replicating protein antigen derived from a tumor cell or from pathogenic organism where CTL response is likely to play an important role in conferring protective immunity in a mammal, with the proviso that the particulate component is not a prokaryotic or eukaryotic cell or a micellar multimicellar, or liposome vesicle composed of detergents or lipids. The non-replicating protein antigen is attached to the particle component through a covalent or non-covalent association to form particulate protein antigen complexes and the complexes are administered to a mammalian host in conjunction with a pharmaceutically acceptable excipient, in a CTL-stimulatory amount. The invention also provides non-replicating vaccines and methods of vaccinating a mammalian host against pathogenic diseases or tumors for CTL immunity.

20 Claims, 10 Drawing Sheets

INDUCING CYTOTOXIC T LYMPHOCYTE RESPONSES

STATEMENT OF RELATED APPLICATION

This application is a continuation-in-part of application U.S. Ser. No. 08/003,233, filed on Jan. 11, 1993, abandoned.

STATEMENT OF GOVERNMENT RIGHTS TO INVENTION

This invention was made with United States government support under Grant R01 AI 31337, awarded by the National Institutes of Health. The United States government therefore has certain rights to the invention.

FIELD OF THE INVENTION

This invention relates to compositions and methods for inducing class I major histocompatibility-restricted cytotoxic T lymphocyte responses in a mammal by immunization with particulate protein antigen complexes comprising non-replicating protein antigen. The invention also relates to vaccine development for cytotoxic T lymphocyte immunity and methods of treating infectious diseases.

BACKGROUND OF THE INVENTION

One of the major immune responses that protects a host from disease, especially from intracellular infection, is the generation of cytotoxic T lymphocytes (CTLs). CTLs kill host cells that are infected and thereby eliminate the production and/or reservoir of the pathogen. CTLs may also control secondary pathogenic effects induced by infectious organisms, for example, the growth of transformed cells. There is abundant evidence that CTLs are critical components in the defense of the host against several viral pathogens, including influenza, POX and Herpes (Blanden, *Transplant Rev.*, 19:56 (1975); Yap et al., *Nature*, 273:238 (1978). Furthermore, CTLs can provide immunity in vivo to retrovirally-induced diseases (Earl et al., *Science*, 234:728 (1986)). There is increasing evidence that CTLs may play a role in protection from human immunodeficiency virus (HIV). For example, CTLs from infected humans and apes can lyse infected cells and inhibit virus production in vitro.

One of the most efficacious and cost effective therapies for the prevention of infectious diseases is the stimulation of specific immune response through vaccination. The need for an effective HIV vaccine is tragically apparent.

Historically, vaccines have been prepared by killing or attenuating a pathogen, such as a virus or bacterium, and then injecting the resulting particles into a patient or host animal. Vaccines have also been prepared by using only a portion of the pathogenic organism, such as a predominantly important protein subunit from a bacterium or virus. While non-living virus particles and subunit vaccines can prime for a class-II restricted antibody response, such non-living vaccines typically do not prime for cytotoxic T lymphocyte immunity.

It is now well established that the tight segregation of the MHC class I pathway of antigen presentation accounts for the failure of most protein-based vaccines to prime CTL responses and is a major obstacle to using such vaccines. Specifically, from the published literature it is known that most antigens in the extracellular fluid are taken up by specialized antigen presenting cells (APCs), processed in an endosomal compartment, and subsequently displayed in association with class II MHC molecules, which elicits an antibody response. In contrast, most exogenous antigens are not presented in association with class I MHC molecules, which is necessary for a class I-restricted CTL response. However, exogenous antigens are presented in association with class I molecules if they are introduced, via experimental manipulations, into the cytoplasm ("cytosol") of cells. It is thought that the antigenic peptides that arise from processing in the cytosol are transported to the endoplasmic reticulum where they associate with class I MHC molecules. The failure of exogenous proteins to be presented in association with class I molecules reflects the inability of these proteins and their degraded endosomal products, to communicate with the appropriate cytosolic compartment, under physiological conditions. As a consequence of this segregation between MHC-class I and class II antigen-presentation pathways, CTLs are selectively targeted to pathologically-affected cells (ie. cells synthesizing abnormal proteins). Uninfected, healthy cells are not at risk of elimination when they encounter antigens in the extracellular fluids.

Despite the generally recognized inability of most antigens to prime CTL response, there have been reports in literature of inducing MHC class I-restricted CTLs with non-replicating antigen in vivo. For example, Zhou et al. have shown that allogeneic splenocytes, MHC-free red blood cells, and synthetic lipid vesicles (liposomes) loaded with chicken ovalbumin (OVA) can elicit an OVA-specific MHC class I-restricted immune response. *J. Immunol.*, 149:1599 (Sep. 1, 1992). Liposomes were also used by Reddy et. al to incorporate soluble proteins of OVA and β-galactosidase for priming a $CD8^+$ CTL response to antigen in vivo in mice. *J. Immunol.*, 148:1585 (Mar. 1, 1992), while Bevan et al. have demonstrated CTL priming against soluble OVA with a cell-associated system *J. Exp. Med.*, 171:377 (1990). Complex adjuvants, such as complete Freund's adjuvant (CFA) have also been used with some measure of success. Bacteria, such as Mycobacterium and Staph aureus have also been included as adjuvants in immunization for CTL response. Randall & Young, *J. Virol.*, 65:719–726 (Feb. 1991).

Immune stimulating complexes (ISCOMS), which are multimicellar complexes of cholesterol, phospholipid, and a saponin, have been used fairly extensively as carriers of subunit vaccines, especially in veterinary applications, and have been shown to induce $CD8^+$ MHC class I-restricted CTL. See, for example, Nadon et al., *Vaccine*, 10:107 (1992); Mowat et al., *J. Immunol.* 72:317–322 (1991); Takahashi et al., *Nature*, 344:873 (Apr. 26, 1990); and Morein, *Nature*, 322:287 (Mar. 17, 1988). Protective class I MHC-restricted CTLs have been also induced in mice by a recombinant influenza vaccine in an aluminum hydroxide adjuvant, which is currently the only adjuvant licensed by the FDA for clinical use in humans. Dillon et al., *Vaccine*, 10:309 (1992).

Although the foregoing preparations have been used to induce class I-restricted CTLs with varying degrees of success, none is without potential disadvantages, and those skilled in the area of vaccination biology continue to seek compositions and methods for inducing CTL responses to non-living proteins to confer protective immunity from pathogenic infection and minimize serious side effects. For example, many of the complex adjuvants that have been shown to induce CTLs in laboratory animals are unacceptable for use in domestic animals and humans because of their potential toxicity. Cell-associated formulations do not represent a practical immunization strategy for human vaccines, given the significant possibility for infectious contamination in the preparation. CFA does not routinely achieve priming, even in mice, and may result in tumor formation and tissue necrosis. Antigen encapsulation in liposomes or in a lipid/detergent-based adjuvant, such as the ISCOM matrix, appears to be the most promising approach for immunizing with non-replicating protein, but even this approach may have drawbacks. For example, the ISCOM matrix includes a saponin as an essential component. Saponins are hemolysins and there is an indication in the literature that at least some saponins may be cytotoxic at immunogenic concentrations. In addition, the FDA imposes stringent stability requirements on formulations for human vaccines, and cell associated formulations, liposomes and the ISCOM matrix are potentially problematic from that standpoint.

It is an object of the present invention to provide new compositions and methods for inducing MHC class I-restricted CTLs with non-replicating antigens.

SUMMARY OF THE INVENTION

This, as well as other objects and advantages, are achieved in accordance with the present invention, which provides pharmaceutical compositions and methods for inducing MHC class I-restricted cytotoxic T lymphocyte responses in a mammalian host by immunization with non-replicating protein antigens. The pharmaceutical compositions of the invention comprise a two-component complex including a particle component, which is not a prokaryotic or eukaryotic cell, or micellar, multimicellar, or liposome vesicle composed of detergents and/or lipids, ranging in size from about 10 nm to about 50 µm, preferably from 0.5 µm to 6 µm, and a non-replicating protein antigen. The non-replicating protein antigen is attached to the particle component through a covalent or non-covalent association to form particulate protein antigen complexes which are formulated with a pharmaceutically acceptable excipient to form the pharmaceutical compositions of the invention. In one embodiment of the invention, the non-replicating protein antigen comprises at least one pathogenrelated protein, especially a bacterial or viral protein. In another embodiment, the non-replicating protein antigen comprises a tumor antigen.

Another embodiment of the invention provides methods for targeting protein antigen into the MHC class I pathway of antigen presentation in a subpopulation of antigen presenting cells that are capable of processing exogenous antigen from the extracellular environment and presenting the processed antigen in association with class I MHC molecules.

In another embodiment of the invention, the particulate protein complexes are used in CTL vaccine development, for example in an assay for identifying potential CTL vaccines from a plurality of candidate complexes.

In yet another embodiment, the invention provides non-replicating vaccines and methods of vaccinating a mammalian host, especially a human being, for CTL immunity.

The invention is useful in vaccination for CTL immunity with protein antigens and in vaccine development.

BRIEF DESCRIPTION OF THE DRAWING

FIGS. 6A and 6B show that the OVA-particles primed CTLs at 90 μg and 18 μg of complex, respectively. FIGS. 6C and 6D show that same amounts of soluble OVA were not effective.

FIGS. 7A shows that the β-gal-particles primed CTLs at 13 μg of the complex. FIGS. 7B and 7C show that same amount of soluble β-gal and ten times the amount of β-gal, respectively, were ineffective.

FIG. 12A shows the results for mice primed only one time; FIG. 12B shows the results for the animals that were reimmunized on day 7. The results show that the particulate protein antigen complex could prime a CTL response, even in immunodeficient animals.

DETAILED DESCRIPTION OF THE INVENTION

Figure 1A:
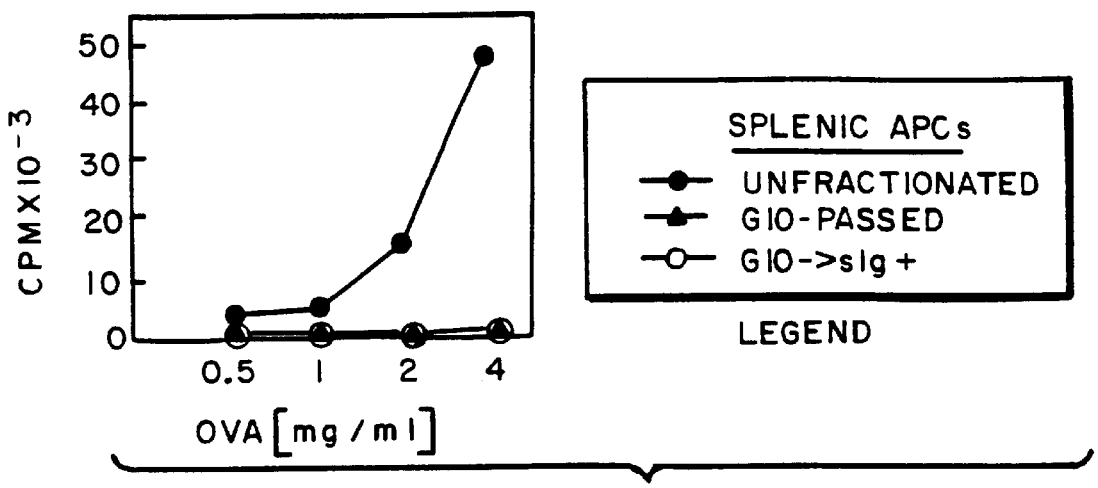
FIG. 1A depicts the results of an antigen presentation assay, which demonstrates that accessory cell depletion from splenic antigen presenting cells removes antigen presenting cells that process and present antigen with class I molecules. The closed circles represent the antigen-presenting activity of unfractionated splenocytes; the closed triangles the antigen-presenting activity of G10-passed spleen cells; and the open circles the activity of sIg+ B cells positively selected from G10-spleen by panning on anti-Ig coated plates. Data are expressed are the mean counts per minute (CPM) of $^3$[H]TdR incorporated by HT-2 cells.

The present invention is based upon our discovery of a normal antigen presenting cell, which is resident in unstimulated lymphoid tissue of mice, that can take up antigens, process them, and present them in association with class I molecules. See, Rock, Science, 249:918–921 (August, 1990). We have now characterized this specialized cell as a macrophage, which expresses both class II molecules and the complement receptor (FcR). Without wishing to be held to any particular theory or mechanism of the invention, it is presently believed that the particulate antigen complexes of the invention are more efficiently targeted to the class I pathway of these antigen presenting cells than soluble protein antigen, especially in vivo, because they are more readily phagocytized.

The particulate antigen complexes of the invention contain two components: a particle component having an average diameter ranging in size of from about 10 nm to 50 μm; and a non-replicating protein antigen. The two components are physically linked through a covalent or a non-covalent association.

The particle component can be formed from almost any material that is not deleterious to the antigen presenting cells or the mammalian host. However, the particle is not a liposome vesicle or a micellar or multimicellar matrix formed of detergents and lipids, e.g. an ISCOM matrix, nor is it a prokaryotic or eukaryotic cell or cell debris. As used herein, the term liposome means a synthetic vesicle or sac composed of a lipid bilayer.

For example, the particle component of the invention can be formed from a natural or synthetic organic polymeric material or an aqueous suspension or emulsion thereof. Particles are preferably formed from biocompatible, natural polymers, such as polysaccharides, including starches, cellulose, pectin, seaweed gums (agar), vegetable gums (arabic etc.) or copolymers thereof, and proteins, including casein, albumin, and keratin. Particles of oligosaccharides, formed of two or more monosaccharides linked by glycoside bonds, can also be used. The copolymer poly (DL-lactide-co-glycolide) is a preferred material, as is latex, an aqueous suspension of a naturally occurring hydrocarbon polymer. Ribonucleic acids, especially DNA, can also be used to form the particle component of the particulate antigen complex of the invention.

Suitable organic synthetic polymers include polystyrene, and lower alkyl hydrocarbons having between 2 and 6 carbons. The particle component can also be formed from a metal, especially one of the transition metals of the Periodic Table Of Elements, including elements 21–29 (scandium through copper), 39 through 47 (yttrium through silver) and 57–79 (lantham through gold) or of oxides of such metals, especially iron oxide.

The materials used to form the particle component can be modified, as necessary, to include chemical linking groups reactive with the amino terminus or the carboxy terminus of a protein antigen, or with any reactive side chain thereof, in accordance with techniques known in the art. Such modified particles, which are typically in the form of beads, are also available commercially. Suitable materials which are available commercially include, but are not limited to, DYNABEADS® available from Dynal, Inc. (Great Neck N.Y.) (paramagnetic, polystyrene beads activated by p-toluenesulfonyl treatment for chemical binding of proteins); BioMag™ iron oxide particles, available for Advanced Magnetics (Cambridge, Mass.); POLYBEAD® microparticles, available from PolySciences, Inc., (Warrington, Pa.)(monodispersed polystyrene latex beads and functionalized microparticles); Spherisorb (TM) silica beads, available from Phase Sep.(Norwalk, Conn.). Particles can also be modified with, an immunoglobulin which in turn can be linked covalently to the protein antigen.

Protein, agarose, and polysaccharide-based beads are preferred materials for in vivo vaccine applications.

The size of the particle component of the particulate protein antigen complex has been found to be an important consideration, regardless of the size of the protein antigen. In general, average diameter of the particle component should be at least about 10 nanometers (nm) and no more than about 50 microns ($\mu$m). Preferably, the average diameter of the particle ranges from about 0.10 $\mu$m to about 10.0 $\mu$m, and most preferably about 0.50 $\mu$m to about 6.0 $\mu$m.

These materials are provided as examples only and are not intended to limit the nature of the particle component to be used in accordance with the present invention. Other materials falling within the specified size ranges that are not deleterious to the target antigen presenting cell or the mammalian host can be used, and other suitable materials will be readily apparent to the skilled artisan.

The protein antigen to be complexed with the particle component can be any protein antigen, especially a protein from a pathogen or tumor cell for which class I MHC-restricted CTLs appear to be important to confer protective immunity. As used herein, the term pathogen means any disease-causing microorganism, including viruses, rickettsia, bacteria, and parasites, especially protozoa and helminths.

In one embodiment, the protein antigen comprises at least one immunogenic protein from a pathogen, preferably from a virus or a bacterium, which is non-replicating.

When the pathogen is a virus, the protein antigen can be killed or inactivated whole virus; it can be a virus-like particle comprising envelope proteins and/or glycoproteins, or it can be protein subunit or fragment thereof from a capsid or envelope antigen or an internal antigen from a virus, in which the virus is a member of families including adenovirus, picornavirus, corona virus, orthomyxovirus, paramyxovirus, herpes virus, retrovirus or papovavirus. Preferably, the protein antigen will be from a virus that causes an infection in which CTLs may play an important role in conferring immunity, such as influenza or parainfluenza virus, retroviruses, including HIV-1, HIV-2 and SIV, POX viruses (e.g., Varicella zoster), Herpes viruses, including Herpes simplex 1 and Herpes simplex 2, respiratory syncytial virus, rabies virus, measles virus, polio virus or rotavirus.

Inactivated, non-living whole virus preparations can be prepared in accordance with any of the techniques known to people skilled in the art, including heat inactivation, and may be used especially in preparing particulate antigen complexes for polio, influenza, rabies, and Japanese B encephalitis viruses. Virus-like particles are recombinantly-produced structural proteins that selfassemble into structures resembling empty virions under defined conditions and are also potential candidates for vaccine development in accordance with the present invention. The preparation and characterization of recombinantly-produced virus-like particles have been described for surface proteins from several viruses, including human papilloma virus type 1 (Hagnesee et al, *J. Virol.*, 67:315 (January 1991); human papilloma virus type 16 (Kirnbauer et al., *Proc. Natl. Acad. Sci.*, 89:12180 (December, 1992); HIV-1 (Haffer et al., *J. Virol.*, 64:2653 (1990), Hu et al.,*J. Virol.*, 179:321 1990); hepatitis A (Winokur, *J. Virol.*, 65:5029 (1991); and human polyoma virus (Rose et al., in press). The teachings of the referenced articles relating to the preparation, characterization, and purification of virus-like particles are hereby incorporated by reference. These virus-like particles, which resemble live virus in external conformation but are non-infectious, may be processed and presented by class I MHC molecules of antigen presenting cells in a manner analogous to that for live virus and are good candidates for vaccine development.

For many viruses, one or more individual antigens may be predominantly important for conferring immunity, including a CTL component, so that vaccines can be comprised of that protein subunit, or immunogenic fragment thereof. One example is the surface antigen of the hepatitis B virus, HBSag, that is secreted from cells and present in the blood of infected human beings. A second example is the influenza hemagglutinin (HA) antigen, which can be chemically removed from the virus capsid or produced recombinantly using techniques that are old and well known in the art.

Protein subunits and fragments can be obtained by conventional techniques, such as proteolysis, chemical treatment, or solubilization and purification of the relevant protein from the native virus, they can be prepared using automated peptide synthesis techniques, or they can be produced by recombinant DNA techniques and then purified in accordance with procedures known to persons skilled in the art. When the antigen is obtained through recombinant DNA techniques, DNA including that encoding the antigen of interest is cloned into an expression vector, such as a vaccinia virus, baculovirus, plasmid, or phage and expressed in a suitable prokaryotic or eukaryotic expression system, in accordance with established protocols. See, Sambrook, Fitsch, & Maniatis, *Molecular Cloning*, Chapters 8 and 9 (second edition, 1989), which are hereby incorporated by reference.

When the protein antigen is from a bacterium, the antigen can be from inactivated bacteria, it can be from a toxin or a capsular polysaccharide, or it can be a subunit antigen. Preferably, the protein antigen is from a bacteria where cellular immunity appears to be important for providing protection against infection or reinfection, for example bacteria causing tuberculosis (*Mycobacteria tuberculosis*); leprosy (*Mycobacterium leprae*), brucellosis (Brucella spp.) and listeriosis (*Lysteria monocytogenes*). Such protein antigens can be prepared readily by persons skilled in the art, by traditional or recombinant DNA techniques.

In yet another embodiment of the invention, the non-replicating protein antigen can be from a parasite where CTL response appears to be important for conferring immunity. Such parasites include members from the class Apicomplexa, which includes Plasmodium species that are the etiologic agents of infectious malaria and Toxoplasmosis gondii, the etiologic agent of toxoplasmosis. Also included are protein antigens from Leischmania species.

Tumor-associated antigens, i.e., antigens associated with neoplastic disease, can also be used as the antigen in the particulate antigen complexes of the invention. Preferably, the tumor antigen will be an antigen associated with human melanoma, colonic carcinoma, breast carcinoma, or renal carcinoma. It has previously been shown, for example, the autologous CTLs recognize a total of six independent antigens on human melanoma cells, which can be used in the particulate protein antigen complexes of the invention. See, Van Der Bruggen, et al., *Science*, 254:1643 (December, 1991).

The linkage between the antigen and the particle of the invention can be formed in one of a variety of ways. What is important is that the linkage is sufficient to physically associate the two components of the complex. The linkage to be used for a given complex will depend upon the composition of the particle and the protein antigen. For some complexes the linkage will best be made by chemical means (covalent linkages), while for other particle complexes, linkage through non-covalent associations, such as adsorption of the protein antigen to the particle component, will suffice.

The elements of the complex can be covalently linked by means well known to persons skilled in the art, including standard dehydration reactions using carbimides or by a large variety of heterobifunctional agents or linkers. Covalent linkages through peptide bonding of the amino or carboxy terminus of the protein antigen or any appropriate amino acid in the side chain thereof with reactive groups on the particle component is a particularly preferred linkage. Particularly useful linkages also include those which generate a disulfide link at one functional group and a peptide link at the other, including N-succidimidyl-3-(2-pyridyldithio) propionate (SPDP) (Pierce Chemicals) (Rockford, Ill.). This reagent creates a disulfide linkage between itself and a cysteine residue in one protein and an amide linkage through the amino group on a lysine or other free amino group on the other component. A large number of disulfide/amide forming agents are known. Other bifunctional linking agents form a thioester rather than a disulfide linkage. The ability to make such linkages is well within the skill in the art, and the skilled artisan can readily identify a suitable linkage for a given complex.

The particulate antigen complexes of the invention are useful in vaccine development with non-living vaccines and are also useful in vaccinating mammalian hosts for CTL immunity. The complexes of the invention may also be useful in the treatment of infectious diseases, such as HIV-1 and HIV-2, where CTL response to infection may play an important role.

For example, the particulate protein complexes of the invention can be used in CTL vaccine development. In one embodiment, the complexes are made as described herein and evaluated for their activity in an in vitro antigen presenting assay similar to the one described in the Examples. The identification method involves obtaining a plurality of potentially immunogenic antigens from a pathogen, such as a virus, for which a CTL vaccine is sought, linking the protein antigens to a particle to form particulate antigen complexes; adding the particulate antigen complexes to a population of antigen presenting cells, including macrophages, and lymphokine secreting CTLs or antigen-specific T—T hybridomas that previously have been stimulated with an appropriate antigen, such as a whole virus; and selecting a complex including a protein antigen recognized by the previously stimulated CTLs. This in vitro assay system enables the identification of active complexes and can also optimize identification of the component of the pathogen recognized by CTLs. The antigen presenting cells used in the antigen presentation assay must include a subpopulation of macrophages that have the ability to take up, process, and present antigen in association with class I MHC. In accordance with the present invention, it has been discovered that mouse bone marrow cells, thymic macrophages, spleen cells, and resident and stimulated peritoneal macrophages all include a subpopulation of macrophages exhibiting this activity, and can therefore be used in the in vitro assay of the invention.

One of several antigen presentation assays known in the art can be used in this in vitro screen. Preferred assays will employ a read out that measures lymphokine or serine esterase production by CTLs or by class I-restricted T—T hybridomas. Alternatively, if the subpopulation of macrophages that have the ability to present exogenous antigen in association with class I can be lysed by CTLs, the read out system can employ a standard chromium release assay well known to those of skill in the art. The preparation of class I restricted T—T hybridomas using a BW5147 cell line transfected to express the CD8 gene has been described in the literature (Rock et al., *J. Immunol.*, 145:804 (1990), the teachings of which are hereby incorporated by reference. These techniques can be used to prepare antigen-specific, class I-restricted T—T hybridomas useful in the screening assays of the invention. Particulate antigens that elicit a strong CTL response in vitro are good candidates for vaccine development for infectious diseases or tumor-associated pathological disorders where the cellular arm of the immune response may be important to confer complete protection.

In another embodiment relating specifically to vaccine development, candidate complexes can also be tested in a suitable animal model, to determine whether a candidate vaccine comprising a particulate protein antigen complex of the invention can confer immunity against infection with the live pathogen or whole tumor cells. The ability of a given particulate antigen complex to confer protective immunity against infectious disease in a animal can be established using challenge assays, such as lethal or sub-lethal challenge assays, known in the art. For example, where the animal model is a laboratory animal such as a mouse or a rat and the antigen is a viral antigen, the animal is immunized with the candidate particulate antigen complex of the invention via a suitable route of administration, such as subcutaneously, intravenously or intraperitoneally, with or without boosting, and subsequently challenged with lethal doses of virus in a suitable carrier. Survival of the immunized animals is monitored and compared to virus-immune positive control and negative control animals, with have been immunized with live virus and soluble antigen, respectively. A lethal challenge assay that can be used is described, for example, in Dillon et al, *Vaccine*, 10:309 (19912).

In another embodiment, the particulate antigen complexes of the invention are used in pharmaceutical compositions that, when administered to a mammalian host in an effective amount, are capable of inducing CTL immunity. In accordance with the present invention, the particulate antigen complexes will have utility in both medical and veterinary applications and can be used therapeutically, as well as prophylactically. The term mammal as used herein includes both human and non-human primates, including chimpanzees and monkeys, and domesticated mammals, such as dogs, cats, rabbits, guinea pigs, pigs, cows, horses, sheep, and goats, as well as common laboratory animals such as mice, rats, and hamsters.

The pharmaceutical compositions of the invention comprise a pharmaceutically acceptable excipient, at least one immunogenic particulate antigen complex of the invention, in which the particulate antigen complex comprises a particle having an average diameter of about 10 nm to about 50 $\mu$m and non-replicating protein antigen, and optionally other ingredients, described supra. The excipient must be pharmaceutically acceptable, in the sense of being compatible with the active ingredient(s) of the pharmaceutical composition and not deleterious to the recipient thereof. Examples of suitable excipients are, for example, water, saline, dextrose, glycerol, ethanol or the like, and combinations thereof. In addition, if desired, the pharmaceutical composition may contain minor amounts of auxiliary substances, such as wetting or emulsifying agents, pH buffering agents, bacteriostat or adjuvants which further enhance effectiveness of the vaccine.

The preparation of such pharmaceutical compositions is well understood in the art. Typically, they are prepared as injectables, either as liquid solutions or suspensions; solid forms suitable for solution in or suspension in liquid prior to injection. The preparation may also be emulsified. The compositions may also be formed for oral delivery, in which case the formulation will normally contain such excipient as, for example, pharmaceutical grades of mannitol, starch, lactose, magnesium stearate, sodium saccharide, cellulose, magnesium carbonate and the like. These compositions can take the form of solutions, suspensions, tablets, pills, capsules, sustained release formulations, and powders.

The compositions of the invention are administrated to a mammal in need of such treatment, such as a mammal at risk of infection from or infected with a pathogenic organism or at risk of developing a tumor-related disorder, in a CTL-stimulatory amount. Administration of the pharmaceutical compositions of the invention may be by any suitable route including oral, nasal, topical and parenteral, with oral and parenteral routes, including subcutaneous, intramuscular, intravenous, and intradermal, being preferred.

By CTL-stimulatory amount is meant that the pharmaceutical composition contains sufficient amount of the particulate protein antigen complex of the invention to induce CTL response to the subject antigen. The precise amount to be administered will vary depending upon the protein antigen, mode of administration selected, and the mammalian host to be immunized.

The invention is more fully described in the following Examples. These Examples are provided for illustrative purposes only and are not meant to limit the invention in any way.

EXAMPLE 1

Exogenous antigens in the extracellular fluids do not gain access to the class I antigen presenting pathway in most cells. However, there is an APC resident in spleen that can process and present exogenous Ags in association with class I molecules. In this Example, we characterize the phenotype of this cell. This APC is of low buoyant density, is adherent to sepharose and glass, and expresses both class II molecules and Fc-receptors. This phenotype identifies this APC as a macrophage. Resident, peptone- and thioglycolate-induced peritoneal macrophages also display this antigen presenting activity. Analysis with CTL clones suggest that this antigen presenting pathway may be active in only a subset of macrophages. A similar antigen presenting activity is also present in dendritic cell-enriched populations from spleen although we cannot rule out the possible involvement of contaminating macrophages. In contrast, B and T cells that are resident in spleen and LPS blasts are unable to present exogenous Ags in association with class I molecules.

Methods And Materials

Mice

C57BL/6 mice, ages 5–8 weeks were purchased from the Jackson Laboratory (Bar Harbor, Me.) or were bred at the Dana-Farber Cancer Institute.

Reagents

Chicken OVA was purchased from ICN Immunobiologicals, Lisle, Ill., or Sigma, St Louis Mo. Isotonic BSA (pathocyte 4) was purchased from ICN Immunobiologicals, Lisle, Ill.

Cell Lines

The RF33.70 (anti-OVA+$K^b$) (14) T cell hybrid has been previously described.

Cell Fractionations and Incubations

Splenocytes were depleted of erythrocytes by treatment with Tris-$NH_4Cl$ and depleted of accessory cells by passage over two successive G10 sephadex columns (Ly et al., *Immunol. Methods*, 5:239 (1974)). B cells were positively selected by panning on rabbit anti-Ig coated dishes. LPS-blasts were prepared by incubating G10-passed splenocytes with LPS (10 $\mu$g/ml) for 72 hrs at 37° C. Splenocytes were fractionated into low (floating above 25% isotonic BSA) and high density fractions by centrifugation on BSA gradients, essentially as previously described (Beller and Unanue, *J. Immunol.*, 118:1780 (1977); Grant and Rock, *J. Immunol.*, 148:13 (1992). In some experiments, low density splenocytes were incubated on sterile petri dishes at 37° C. and glass-nonadherent cells collected after 2 hrs and the remaining cells incubated for another 18–24 hrs; nonadherent cells were collected and adherent cells were harvested at the later time points by scraping. In some experiments low density cells, or 24 hr glass-nonadherent low density cells were further fractionated by rosetting with sheep red blood cells (SRBCs) sensitized with rabbit anti-SRBC Ab (kindly provided by Dr. G. Sunshine, Tufts University, Boston, Mass.), as previously described (Steinman et al. *J. Exp. Med.*, 149L:1 (1979); Sunshine et al., *J. Exp. Med.*, 152:1817 (1980)). Peritoneal exudates were harvested by lavage from naive mice or mice injected three days earlier with approximately 1.5 mls of thioglycolate or peptone broth. In some cases, peritoneal exudate cells were cultured for 18–24 hrs on flat bottom plastic microtiter wells and then separated into adherent and nonadherent fractions.

Cell Culture

Media was RPMI 1640 (Irvine Scientific, Santa Ana, Calif.) supplemented as previously described (Rock et al, *J. Immunol.*, 145:804). T—T hybridoma cultures were prepared as previously described (Rock et al., *J. Immunol.*, 145:80414). Briefly, microcultures were prepared with $5-10 \times 10^4$ T—T hybrids in the presence or absence of APCs, and with/or without antigen in 200 ml media in flat bottom microtiter wells in duplicate. The precise culture constituents are detailed in the respective experimental protocols. Dose response curves were generated by titrating the number of APCs per well in the presence or absence of a constant amount of Ag, or by titrating the concentration of Ag with a constant number of APCs per well. After 18–24 hours incubation at 37° C., a 100 ml aliquot of supernatant was removed and subjected to freeze-thawing.

Mitogen responsiveness was determined by incubating splenocytes ($2 \times 10^5$ cells/well) with or without Con A (5/ml) or LPS (10 m/ml) in flat bottom microtiter plates in triplicate. After 48 hrs incubation at 37° C., the incorporation of $^3$H-thymidine into DNA was determined.

Lymphokine and Cytotoxicity Assays

IL-2 content in T cell hybridoma culture supernatants was measured with a quantitative bioassay with HT-2 cells (Watson, *J. Exp. Med.*, 150:1510 (1979)) as previously described (Kappler et al., *J. Exp. Med.*, 153:1198 (1981); Rock and Benacerraf, *J. Exp. Med.*, 157:1618 (1983)). In the absence of antigenic stimulation the CPM was usually $<1 \times 10^3$. Cell-mediated cytotoxicity was measured using $^{51}$Cr release assays as previously described (Rock, *J. Immunol.*, 145:804)

Results

Accessory cell-depletion removes APCs that process and present exogenous Ags with class I molecules.

In our initial studies, we demonstrated that the splenic APCs that process and present exogenous Ags with class I molecules expressed class II molecules. (Rock, K. L., S. Gamble, and L. Rothstein. 1990 *Science* 249:918). In spleen, class II molecules are expressed on B lymphocytes, dendritic cells and macrophages. The latter cells bind to and can be efficiently removed by incubation with G10 sephadex. (Ly, I. A., and R. I. Mishell. 1974. *J. Immunol. Meth.* 5: 239). In this experiment, we demonstrated that accessory cell depletion removes APC that process and present exogenous antigen with class I molecules.

Cultures were prepared with RF33.70 T cell hybrids (anti-OVA+K$^b$, $10^5$/well), APCs (splenocytes) ($10^6$/well) and with or without the concentration of OVA indicated in FIG. 1A, in flat bottom microtiter wells (200 ml) in duplicate, as described in the Methods And Materials. Unfractionated splenocytes (closed circles in FIG. 1A), G10-passed splenocytes (closed triangles) or sIg+ B cells positively selected from G10-passed spleen by panning on anti-Ig-coated plates (open circles) were used as a source of APCs. After 18 hrs incubation at 37° C., an aliquot (100 µl) of culture supernatant was removed, freeze-thawed, and assayed for IL-2 content with HT-2 cells. Data are expressed as the mean CPM of $^3$H-thymidine incorporated by HT-2 cells. As a control for the functional integrity of the T and B lymphocytes in the fractionated cell populations, these cells ($2 \times 10^5$/well) were cultured with Con A (5 mg/ml) or LPS (10 mg/ml) in flat bottom microtiter wells (200 ml) in triplicate. After 48 hrs incubation the mean CPM of $^3$H-thymidine$\times 10^{-3} \pm$SEM incorporated for unfractionated, G10-passed and G10->sIg$^+$ cells stimulated with Con A was 274±9.2, 260±8.1 and 7.4±0.8, respectively, and stimulated with LPS was 387±13.4; 416±14.4; 345±19.2, respectively; the CPMs without mitogen were $<3 \times 10^{-3}$.

As shown in FIG. 1A, passage of splenocytes over a C10 column markedly decreased the ability of these cells to present exogenously-added OVA to the OVA+K$^b$-specific T cell hybrid, RF33.70. The percentages of B (sIg$^+$) and T (Thy-1$^+$) cells were not appreciably altered by passage over sephadex as assessed by immunofluorescence and flow fluorocytometry (data not shown). Furthermore, the B cells in the G10-fractionated spleen appeared to be functionally competent, as their responses to LPS stimulation were similar to controls, as expected. Similar results were obtained when sIg+ cells from G10-passed spleen and positively selected by panning (FIG. 1A). These results suggest that the majority of B lymphocytes in spleen are incapable of presenting exogenous OVA in association with class I molecules. This conclusion is further supported by experiments with density-fractionated APCs that are described below.

The exogenous Ag-class I APC in spleen is enriched in MØ/dendritic cell populations.

Macrophages (MØ) and dendritic cells have low buoyant density and can be enriched by isopycnic centrifugation. (Beller, D. I., and E. R. Unanue. 1977 *J. Immunol.* 118:1780; Steinman, R. M., G. Kaplan, M. D. Witmer, and Z. A. Cohn. 1979 *J. Exc. Med.* 149:1). In this experiment, we demonstrated that splenic APCs that present exogenous OVA in association with class I MHC molecules are greatly enriched in the low density fractions of spleen. See FIG. 1B.

Figure 1B:
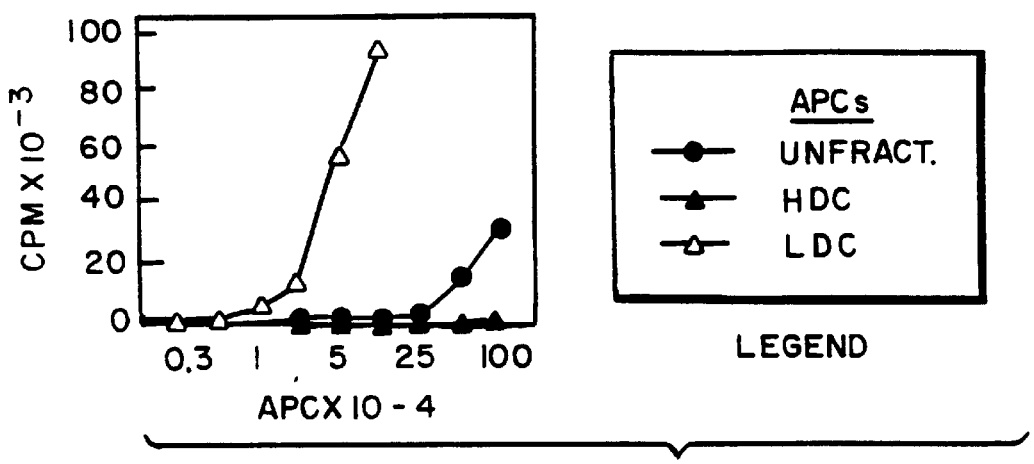
FIG. 1B depicts the results of an antigen presenting assay demonstrating that cells in the low buoyant density fraction of fractionated splenocytes are enriched for antigen presenting cells that can process and present exogenous antigen, in this case, chicken ovalbumin (OVA) with class I MHC. The closed circles represent antigen presentation by unfractionated splenocytes; the closed triangles represent the activity of splenocytes in the high density fraction; and the open circles represent the activity of splenocytes in the low density fraction. The data are expressed as in FIG. 1A.

Splenocytes were fractionated by centrifugation on discontinuous BSA density gradients, as described in the Materials and Methods section. In this experiment, 1.4% of the splenocytes were recovered in the low density fraction. Cultures were prepared as described above and contained RF33.70 T cell hybrids (anti-OVA+K$^b$, $10^5$/well), ±OVA (2 mg/ml) and, as a source of APCs, the number of unfractionated (closed circle), high density (closed triangle) or low density (open triangle) splenocytes, as indicated in FIG. 1B. Cultures were otherwise prepared and handled as described above.

One and one half to five percent of splenocytes were recovered in the low density fraction and, as illustrated in FIG. 1B, there was a corresponding 20 to 40-fold enrichment in the APC activity. Most B lymphocytes and virtually all T lymphocytes are present in the higher density fractions of spleen.

Dendritic cells and macrophages differ in the expression of Fc-receptors and the Fc-receptor has been used to fractionate these two cell populations through resetting with antibody (Ab) -coated erythrocytes. Therefore, we incubated the low density fraction of spleen with Ab-coated erythrocytes and examined the activity of resetting and nonrosetting populations.

Briefly, splenocytes were fractionated by centrifugation on BSA density gradients and 3.8% of cells were recovered in the low density fraction. This fraction is represented by the open triangles in FIG. 1C. The low density cells were then incubated with SRBCs sensitized with rabbit anti-SRBC Ab and the resetting (FCR+, open circle) and non-rosetting (FCR–, closed triangle) cells separated by centrifugation on ficoll-hypaque gradients. The erythrocytes were subsequently lysed by treatment with tris-$NH_4Cl$. Cell recoveries were: 47% resetting with Ig-sensitized SRBCs and 53% non-rosetting; 4.6% of LDCs rosetted with unsensitized SRBCs. The APC activity of the various fractionated and unfractionated cell populations was assayed in cultures prepared and assayed as described above.

Figure 1C:
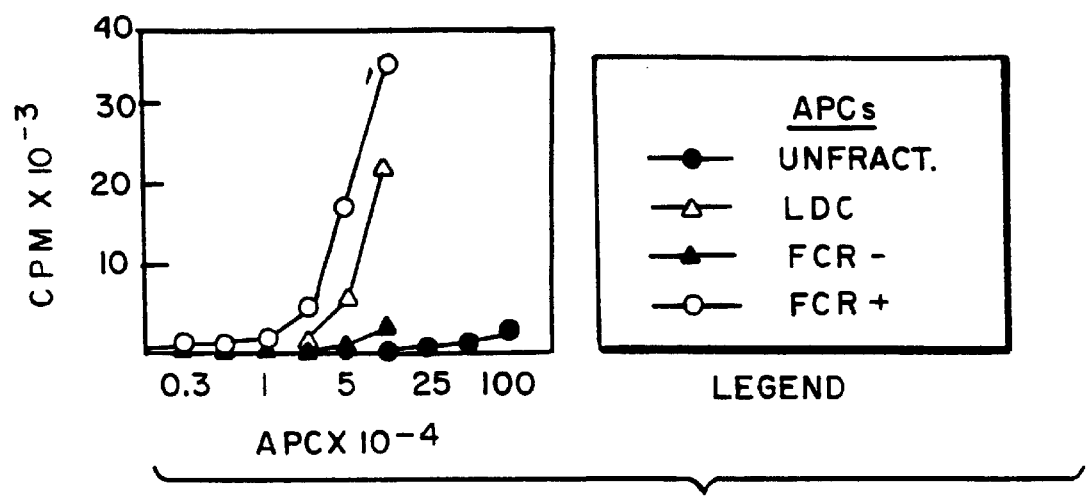
FIG. 1C depicts the results of an antigen presentation assay which demonstrates that resetting cells in the low buoyant density fraction of fractionated splenocytes are enriched for antigen presenting cells that can process and present exogenous antigen in association with class I MHC molecules activity. The closed circles represent antigen presentation activity of unfractionated splenocytes; the open triangles represent the activity of the cells recovered in the low density fraction; the closed triangles represent the antigen presenting activity of non-rosetting cells in the low density fraction; and the open circles represent the resetting cells. Rosetting was obtained by incubating cells recovered in the low density fraction with sheep red blood cells sensitized with rabbit anti-sheep red blood cell antibodies. Data are expressed as in FIG. 1A.

As shown in FIG. 1C, the antigen presenting cells capable of presenting soluble antigen in association with class I MHC (sometimes hereinafter referred to as "ExAPC/I") were positively-selected by binding to Ab-sensitized erythrocytes. Approximately 50% of the low density cells were recovered in this resetting fraction. This fractionation was dependent on the SRBC-bound Ab since few cells (<5%) were recovered when low density cells wee rosetted with unsensitized erythrocytes. We also found reduced, but detectable, ExAPC/I activity in the nonrosetting APC population.

We next examined the adherence properties of the APCs in the low density fractions of spleens that present OVA in connection with class I MHC.

Low density splenocytes were prepared as described above and an aliquot was incubated on glass petri dishes. After incubation for 2 hrs at 37° C., the nonadherent cells were collected. The 2 hr adherent cells were cultured for another 22 hrs and then fractionated into nonadherent and adherent fractions. The APC activity of the various fractionated and unfractionated cell populations was assayed with RF33.70 cells, ±OVA (4 mg/ml) in cultures prepared and assayed as described, except that the unfractionated LDC and 2 hr nonadherent LDC were added to the microtiter plates and incubated for 24 hrs (in parallel to the group incubated on glass for 24 hrs) before the addition of the T—T hybrids and Ag; using this experimental design all APC population were cultured for the same length of time.

Figure 2:
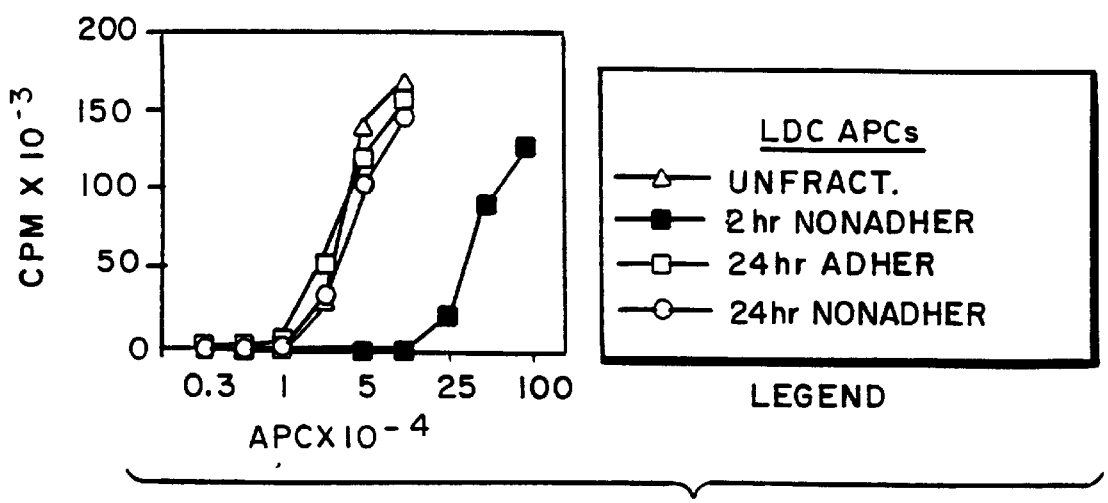
FIG. 2 depicts the results of an analysis of the adherence properties of the antigen presenting cells that present exogenous OVA with MHC class I. The antigen presenting activity of the various fractions, i.e., unfractionated (open triangles), 2 hr nonadherent cells (solid squares), 24 hr adherent (open squares) and 24 nonadherent (open circles) was assayed with RF33.70 T—T hybridomas with or without OVA (4 mg/ml) in cultures prepared and assayed as described, except that the unfractionated low density cells and 2 hr nonadherent cells were added to microtiter plates and incubated for 24 hr before the addition of the T—T hybrids and antigen.

As shown in FIG. 2, the ExAPC/I present in the low density fractions of spleen were adherent to glass (2 hr incubation); when the 2 hr glass-adherent cells were cultured for 24 hrs, the APC activity could be recovered in both released and adherent populations. See FIG. 2. The latter population is enriched for macrophages. The cells that detach from glass during the 24 hour incubation have been previously reported to be composed of both dendritic cells and macrophages. (Steinman, R. M., G. Kaplan, M. D. Witmer, and Z. A. Cohn. 1979 *J. Exp. Med.* 149:1; Sunshine, G. H., D. R. Katz, and M. Feldmann 1980. *J. Exp. Med.* 152:1817).

The adherence properties and expression of FcR strongly suggest that at least some MØs can present exogenous Ags in association with class I. This conclusion is supported by analyses of peritoneal macrophages described below. The finding that this APC activity is somewhat enriched in cell fractions that should be enriched in dendritic cells (FIG. 2) may indicate that cultured dendritic cells also participate in this response, however, we cannot rule out the potential contribution of contaminating MØs.

Activated B cells do not present exogenous Ag in association with class I MHC molecules.

Activation of B lymphocytes increases their ability to present antigens to class II MHC-restricted T cells (Chesnut, P. W., and H. W. Grey. 1986, *Adv. Immunol.* 39: 51). To directly examine the antigen presenting cell activity of activated B cells, we stimulated G10-passed splenocytes with lipopolysaccharide (LPS), as described below.

G10-passed splenocytes were cultured with LPS (10 μg/ml). After 72 hrs incubation at 37° C., lymphoblasts were isolated by centrifugation on ficoll-hypaque. The APC activity of the LPS blasts (closed circle in FIG. 1D) or thioglycolate-induced PECs (open circle in FIG. 1D) was assayed in cultures with RF33.70 cells and OVA (4 mg/ml) as described. As a positive control, PEC APCs were added to parallel cultures and presented with exogenous OVA to RF33.70.

Figure 1D:
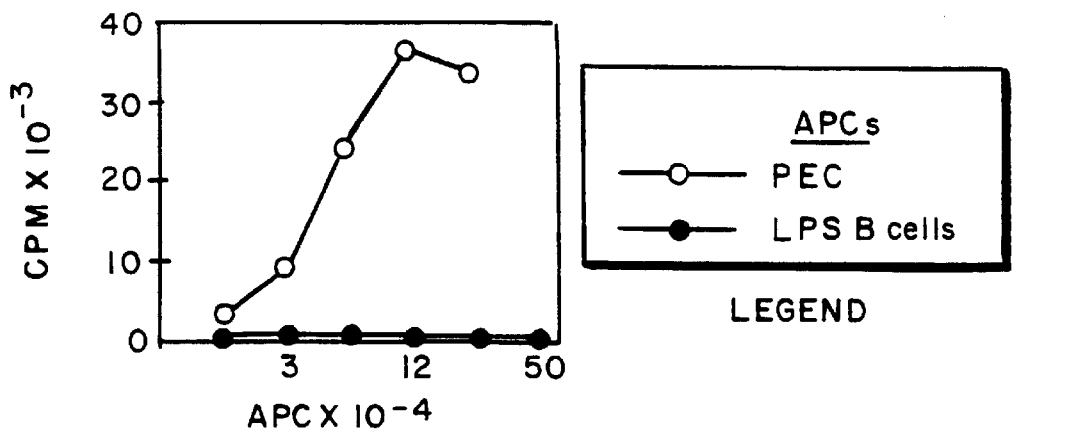
FIG. 1D depicts the results of an antigen presentation assay demonstrating that activated B cells do not present exogenous antigen with class I MHC molecules. In this experiment, G10-passed splenocytes were stimulated with lipopolysaccharide (LPS) prior to the HT-2 assay. The closed circles represent the antigen-presenting activity of the LPS and the open circles the activity of thio-glycolate induced peritoneal exudate cells (PECs). Data are expressed as the mean counts per minute (CPM) of $^3$[H]TdR incorporated by HT-2 cells.

As shown in FIG. 1D, LPS blasts failed to present exogenous OVA to RF33.70.

Peritoneal macrophages can also present exogenous Ag in association with class I MHC molecules.

Macrophages are normally present in the peritoneal cavity and can be recruited by the injection of thioglycolate and peptone into this site. We examined the activity of the cells found in the peritoneum under these conditions. The results are illustrated in FIGS. 3A and 3B.

In this experiment, cells were obtained by peritoneal lavage from naive mice or mice injected three days earlier with thioglycolate or peptone broth. The APC activity of these PECs and unfractionated splenocytes was assayed in cultures with RF33.70 and OVA (4 mg/ml) that were prepared and assayed as described. Thioglycolate-induced PECs were incubated on plastic microtiter wells for 18 hrs at 37° C. after which time the groups indicated in FIG. 3A were separated into adherent and nonadherent cells. The APC activity of these cells was then assayed in cultures with RF33.70 cells and the indicated titration of OVA as described for FIG. 1. The CPM from groups without OVA was <1300.

Figure 3A:
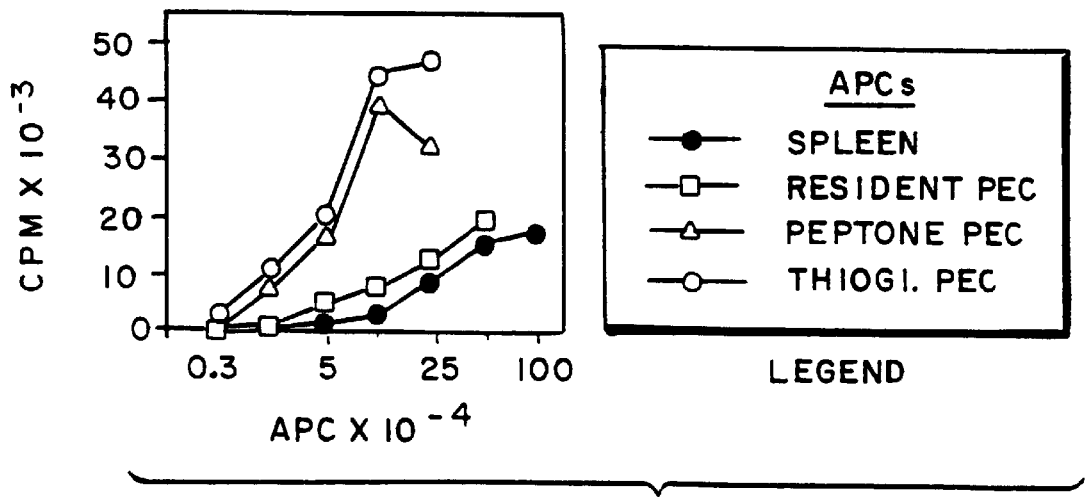
FIG. 3A depicts the results of an antigen presentation assay demonstrating that antigen presenting cells normally present in the peritoneal cavity can present exogenous antigen (OVA) with class I molecules. The solid circles represent the antigen presenting activity of unfractionated spleen cells; the open squares represent the antigen presenting activity of resident peritoneal exudate cells (PECs); the open triangles represent the antigen presenting activity of peptone induced PECs; and the open circles represent the activity if thioglycolate-induced PECs.
Figure 3B:
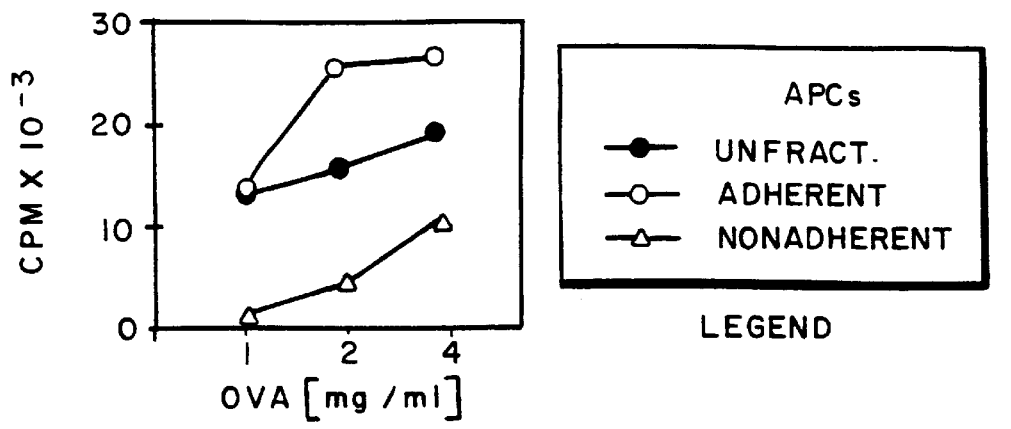
FIG. 3B depicts the results of an antigen presentation assay demonstrating that the antigen presenting cells normally present in the peritoneal cavity that can present exogenous antigen with class I molecules are adherent to plastic. The solid circles represent the antigen presenting activity of unfractionated spleen cells; the open triangles represent the antigen presenting activity of the non-adherent PECs; and the open circles represent the activity of the adherent PECs.

As shown in FIGS. 3A and 3B, the resident cells in the peritoneal cavity can present exogenous OVA to RF33.70 cells. Peritoneal exudates, induced with either thioglycolate or peptone were enriched in cells with this activity, as shown in FIG. 3A. These APCs were adherent to plastic (FIG. 3B). The plastic-nonadherent APC fractions were less active in this assay system. These findings lend further support to the conclusion that MØs can present exogenous Ags in association with class I and indicate that this property is not limited to APCs resident in spleen.

EXAMPLE 2

In this experiment, we explored whether antigen could be more efficiently targeted to the subpopulation of antigen presenting cells described in Example 1 for uptake and entry into the class I pathway by preparing several different complexes of the OVA protein and assaying the ability of the complexes to be presented by class I by different APCs, as described below.

Experiment A.

In this experiment, chicken OVA was covalently coupled with iron oxide particles to form a particulate antigen complex, and APC presentation of the complex by class I MHC molecules was compared to that for uncomplexed, soluble OVA. The chicken OVA, purchased from ICN Immunobiologicals, was covalently coupled to BIOMAG (TM) magnetized iron oxide particles which are coated to provide amino groups (average diameter, 1 μm)(Advanced Magnetics, Cambridge, Mass.) in accordance with the manufacturer's instructions for attaching proteins using glutaraldehyde as the coupling agent. See also, Weston & Avrameas, *Biochem. Biophys. Res. Comm.*, 45:1574 (1971). Briefly, The BioMag suspension of iron oxide particles was first activated with glutaraldehyde. 10 ml of BioMag was transferred to a flat-bottom reaction flask which comfortably holds 50 mL. The coupling buffer (0.01M pyridine) was added to a volume of about 50 ml, the flask was shaken vigorously, after which the BioMag particles were separated magnetically. The liquid in the flask was then aspirated, leaving the BioMag as a wet cake on the container wall. The washing procedure was then repeated with three more additions with the coupling buffer, with the contents of the flask being shaken well after each addition of the buffer.

After the final aspiration, 20 ml of 5% glutaraldehyde was added to the wet BioMag cake, the flask was shaken vigorously, and the flask then agitated at room temperature for three hours. After three hours, the BioMag was magnetically separated and the unreacted glutaraldehyde removed by aspiration. 50 ml of coupling buffer was then added to the flask and the flask was vigorously shaken. The procedure was repeated a total of four times, and the final volume of coupling buffer was aspirated, leaving the activated BioMag as a moist cake on the sides of the flask.

Following activation, 10–18 mg of OVA was added to 10 ml of coupling buffer and added to the BioMag cake and the mixture shaken vigorously. The flask was then agitated overnight at room temperature and the following day the OVA/BioMag complexes were magnetically separated and the contents of the flask aspirated. 50 ml of glycine quenching solution was then added and the contents of the flask were shaken vigorously. After quenching, approximately 50 ml of coupling buffer was added to the BioMag cake, the flask shaken vigorously, and the contents separated magnetically. This washing procedure was repeated four times.

Figure 4A:
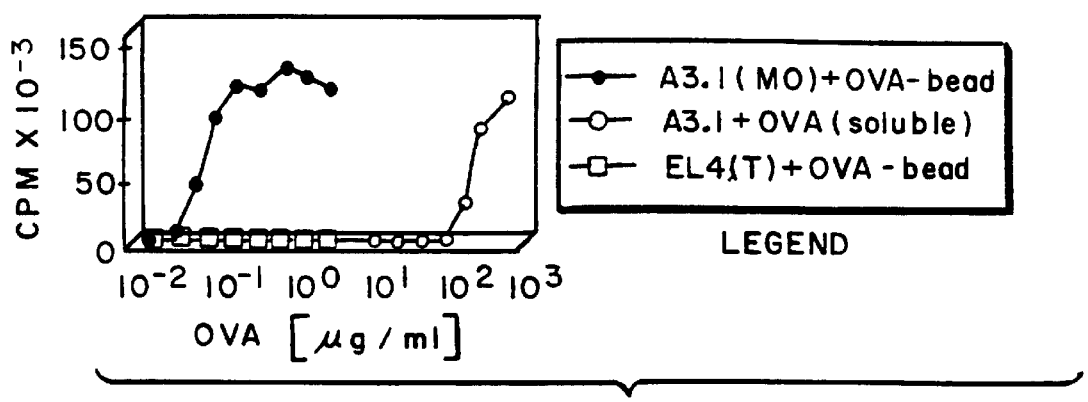
FIG. 4A depicts the results of an antigen presenting assay demonstrating that covalent linkage of antigen to an iron oxide particle dramatically increases the antigen presenting efficiency of a macrophage clone, A3.1, that presents soluble antigen in association with class I MHC.

Separate cultures were then prepared with RF33.70 T—T hybridomas ($10^5$ hybrids per well), as described in Example 1, various APCs ($10^5$ APCs per well) and with varying concentrations OVA or OVA-iron oxide particle, as indicated in FIG. 4A, in flat bottom microtiter wells (200 $\mu$l) in duplicate. Antigen presenting cells were A3.1, (a macrophage clone derived by retroviral immortalization of murine bone marrow cells, followed by selection of an immortalized clone that exhibited the phenotype and antigen presenting capability of the above-described antigen presenting cells) and EL4, a readily available T cell tumor which, like most cells, is unable to present exogenous antigen with class I MHC molecules.

Retroviral immortalization of bone marrow macrophages was achieved substantially as described in Blasi et al., *Nature*, 318:667 (December 1985), which is hereby incorporated by reference.

After incubation for 18 hours, 37° C., an aliquot (100 $\mu$l) was removed from each well and assayed for IL-2 content with HT-2 cells, as previously described.

The results of the experiment are illustrated in FIG. 4A, in which the data represent the mean counts per minute (CPM) of tritiated thymidine incorporated by HT-2 cells ($5\times10^3$) for the duplicate cultures. As illustrated in the Figure, the OVA-iron oxide particle complex (closed circles in FIG. 4A) was presented almost 10,000 fold more efficiently that soluble antigen (open circles) by the macrophage clone, A3.1. EL4 cells, which are not phagocytic and do not present exogenous antigen with class I, were unable to present the particulate protein antigen or the soluble antigen (open squares in FIG. 4A).

Experiment B.

This experiment was similar to the one described in Experiment 2A above, except that, in addition to linking OVA to the iron oxide beads, OVA was also linked to a different particle type, a silica bead, having an average diameter of about 5 $\mu$m.

OVA protein was linked to 5 $\mu$m silica beads, available from Phase Separation (Norwalk, Conn.) by mixing the protein antigen and the 5 $\mu$m beads, in accordance with the manufacturer's instructions. Briefly, the silica beads and OVA protein were mixed in 0.5% deoxy chololate (DOC) in 10 mM Tris-phosphate buffered saline (TBS) and dialyzed at 4° C. for approximately 36 hours to remove the detergent. Ratios used were 600 $\mu$g protein per $10^7$ beads and 5 nm lipid per $10^7$ beads with 2 to $20\times10^6$ beads. Dialysis was against the 0.6 L TBS in a sterile tissue culture flask containing SM-2 biobeads (BioRad, Richmond, Calif.) prepared in accordance with the manufacturer's instructions and used 1 gm per ml of sample being dialyzed, as a detergent absorbent. The flask was placed on an agitating platform to keep the beads in suspension during dialysis. After 24 hours of dialysis, 5 mM lf $CaCl_2$ was added to the dialysis buffer. Dialysis tubing was treated in boiling water and closed with clips after sample addition to exclude air.

After dialysis, the dialysis bag was cut open, and the beads were removed and washed several times in sterile medium and then stored at 4° C. until added to the culture.

Cultures with the particulate-OVA complexes were then prepared as described above and, after 18 hours incubation under the conditions described, supernatants were removed and assayed for IL-2 activity, also as described.

Figure 4B:
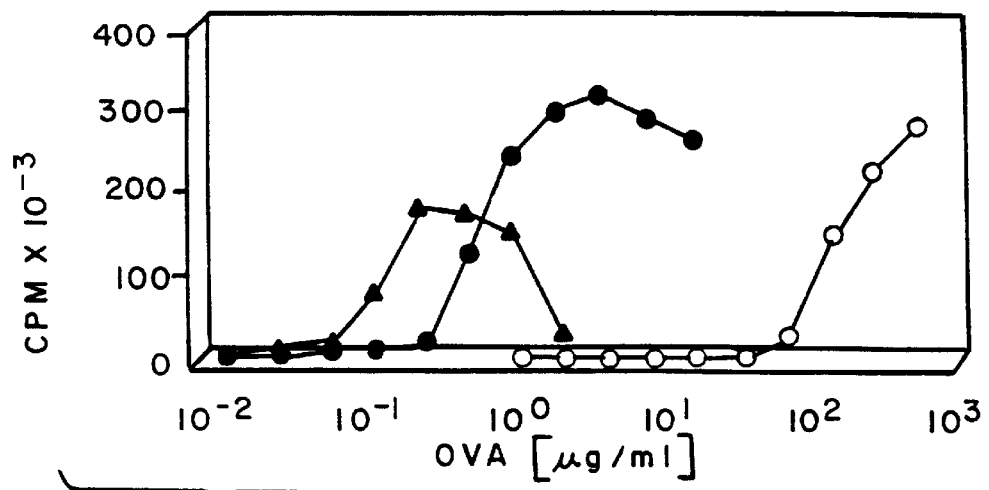
FIG. 4B depicts the results of an antigen presenting assay demonstrating that linkage of antigen to iron oxide or silica particles dramatically increases the antigen presenting efficiency of a macrophage clone, A3.1, that presents soluble antigen in association with class I MHC.

The results of this experiment are set forth in FIG. 4B, in which the open circles represent the activity of soluble OVA in the antigen presenting assay; the closed triangles represent the activity of the OVA-silica complex; and the closed circles, the activity of the OVA-iron oxide complex. These results show that a different type of particle was active in the particulate antigen complex in inducing CTL response. As illustrated in the Figure, the OVA-iron oxide particle complex was once again presented almost 10,000 fold more efficiently than soluble antigen by the macrophage clone, A3.1; the OVA-silica complex was also presented with much greater efficiency.

Experiment C.

This experiment was similar to the one described in Experiments A and B above, except that the OVA was adsorbed to polystyrene microspheres.

OVA was covalently linked to POLYBEAD (R) polystyrene microspheres (average diameter 3 $\mu$m; 2.5% solids—latex) (Polysciences, Inc. Warrington, Pa.), in accordance with the manufacturer's instructions. Briefly, the POLYBEADS were suspended and washed twice in buffer (0.1M borate, pH 8.5), spun down, and then resuspended two times.

2–3 mg/ml of OVA was added to the mixture and the mixture was agitated overnight. The following day, the beads were collected by centrifugation and washed twice in buffer containing 0.1% BSA.

Cultures were then prepared as described above and, after 18 hours incubation under the conditions described, supernatants were removed and assayed for CTL activity, also as described.

Figure 4C:
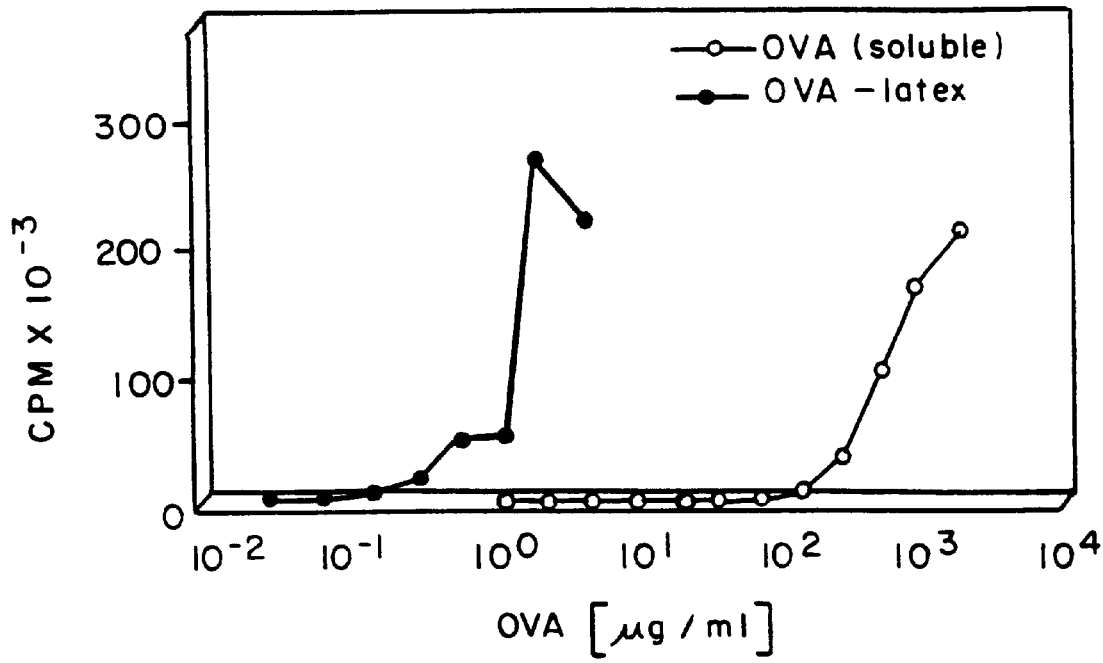
FIG. 4C depicts the results of an antigen presenting assay demonstrating that non-covalent linkage of antigen to latex particles dramatically increases the antigen presenting efficiency of a macrophage clone, A3.1, that presents soluble antigen in association with class I MHC.

The results of this experiment are set forth in FIG. 4C, in which the open circles represent the activity of soluble OVA in the antigen presenting assay and the closed circles represent the activity of the OVA-latex complex. These results show that a different type of particle and linkage were active in the particulate antigen complex in inducing CTL response. As illustrated in the Figure, the OVA-latex particulate antigen complex was more efficiently presented by the macrophage clone, A3.1 than soluble OVA.

EXAMPLE 3

This Example demonstrates that particulate antigen is presented by normal antigen presenting cells with much greater efficiency than soluble antigen.

The Experiments described in Example 2 were all conducted with the A3.1 immortalized macrophage clone. We therefore wished to determine whether normal antigen presenting cells would also exhibit greater efficiency in presenting particulate antigen complexes with class I MHC molecules.

In this Example, the antigen presenting cells were peritoneal exudate cells (PECs) obtained from mice after intraperitoneal injection with about 1.5 mls of thioglycolate media. Peritoneal exudates were harvested by lavage after 72 hours and used in and assay performed substantially in accordance with Example 2A.

Chicken OVA was coupled with BIOMAG iron oxide particles as described in Example 2, to form a particulate antigen complex, and APC presentation of the complex by class I MHC molecules was compared to that for uncomplexed, soluble OVA. Briefly, chicken OVA, (ICN Immunobiologicals), was covalently coupled to BIOMAG (TM) magnetized iron oxide particles in accordance with the manufacturer's instructions for attaching proteins. Separate cultures were then prepared with RF33.70 T—T hybridomas ($10^5$ hybrids per well), as previously described, PEC APCs ($10^5$ APCs per well) and with varying concentrations OVA or OVA-iron oxide particle, as indicated in FIG. 5, in flat bottom microtiter wells (200 $\mu$l) in duplicate.

After incubation for 18 hours, 37° C., an aliquot (100 $\mu$l) was removed from each well and assayed for IL-2 content with HT-2 cells, as previously described.

Figure 5:
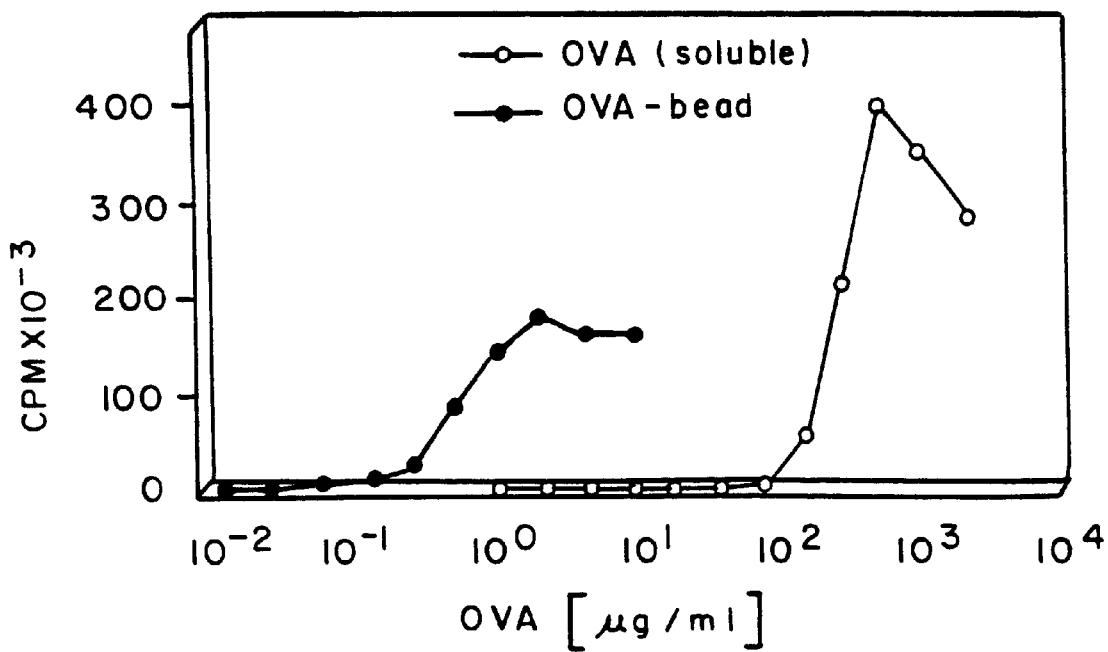
FIG. 5 depicts the results of an antigen presenting assay demonstrating that the covalent linkage of antigen (OVA) to an iron oxide particle dramatically increases the antigen presenting efficiency of thioglycolate-induced PECs.
Figure 6A:
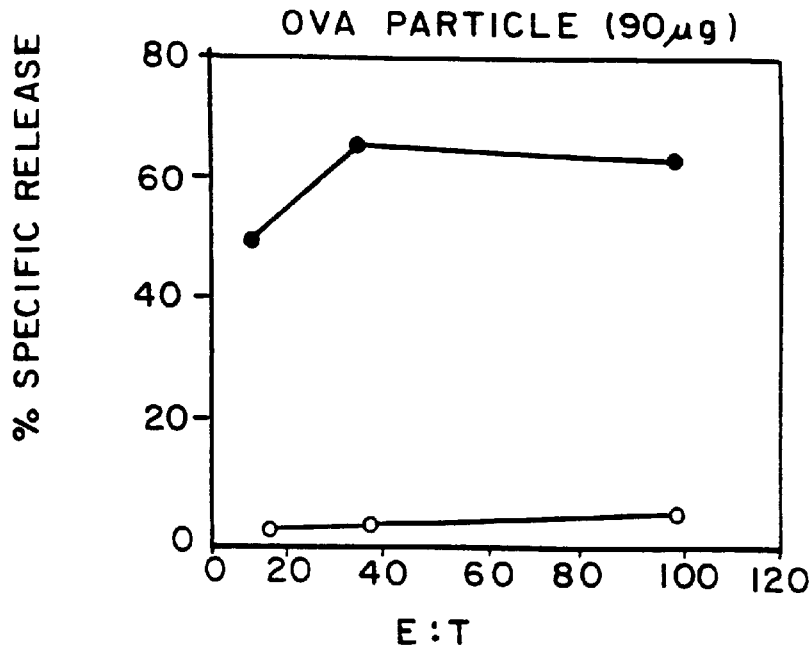
FIG. 6A through FIG. 6D depicts the results of a chromium release assay which demonstrates the ability of particulate protein antigen complexes to prime CTL responses in vivo. C57BL/6 mice were injected subcutaneously with the indicated antigen preparations (OVA particle=OVA covalently linked to iron oxide), with the amount of antigen indicated at the top of the Figures. Seven days later, the animals were sacrificed and splenocytes restimulated in vitro with irradiated EG7 cells. After five days of culture, the cells were tested for their ability to lyse $^{51}$Cr-labeled EL4 cells or EG7 cells. The percent specific release of chromium was measured for the indicated effector to target ratios (E:T).
Figure 6B:
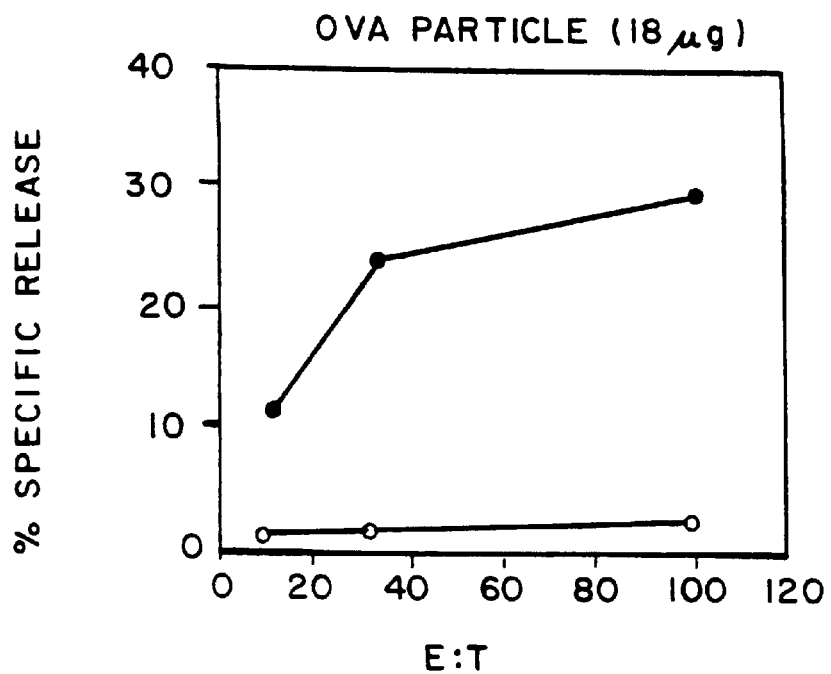
Figure 6C:
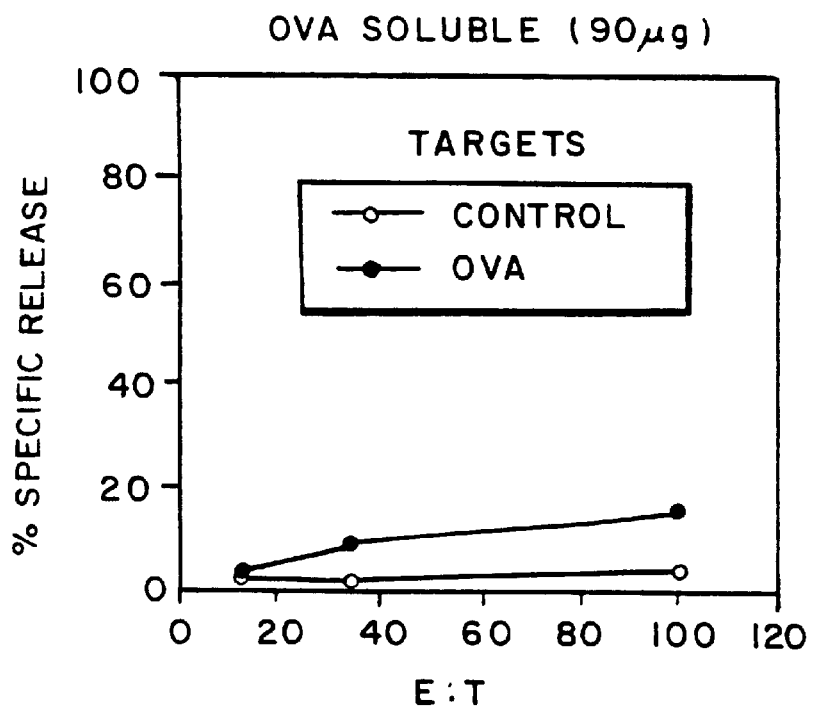
Figure 6D:
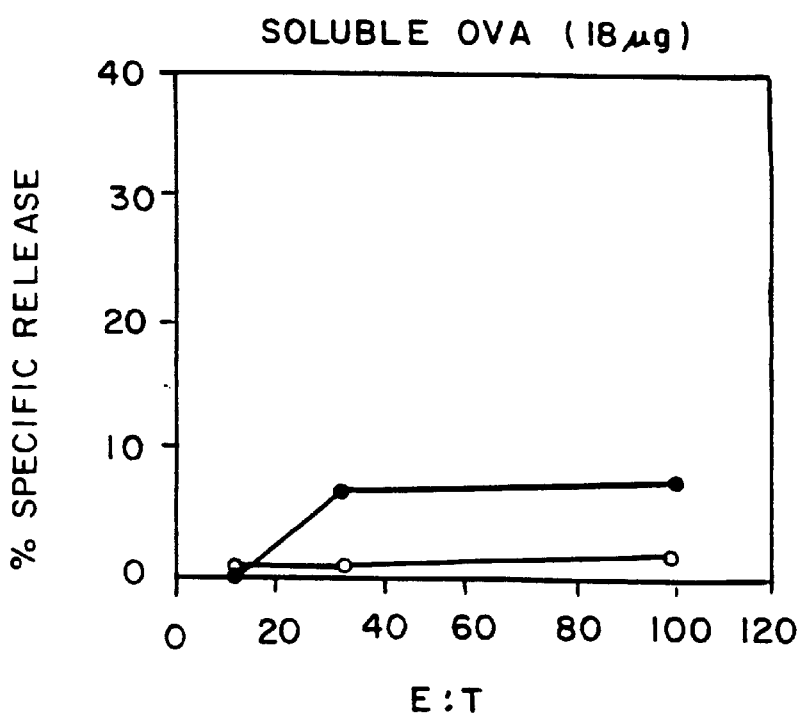

The results of the experiment are illustrated in FIG. 5, in which the data represent the mean counts per minute (CPM) of tritiated thymidine incorporated by HT-2 cells ($5 \times 10^3$) for the duplicate cultures. Open circles represent the activity of soluble OVA in the antigen presenting assay; closed circles represent the OVA-iron oxide complex. As illustrated in the Figure, the OVA-iron oxide particle complex was presented by the PEC APCs much more efficiently than soluble OVA.

EXAMPLE 4

This Example demonstrates the ability of particulate whole protein antigen complexes to prime antigen-specific CTL responses in vivo.
Experiment A.

OVA-iron oxide particles and soluble OVA were prepared as described in Example 2A, formulated with phosphate buffered saline (PBS), and separately injected subcutaneously into both flanks of C57Bl/6 mice, purchased from the Jackson Laboratory, Bar Harbor, Me., or bred at the Dana-Farber Cancer Institute (Boston, Mass.). The amount of protein antigen complex injected was either 90 $\mu$g or 18 $\mu$g.

Seven days following the injections, the mice were sacrificed and their spleen cells removed. Spleen cells ($30 \times 10^6$) were restimulated in vitro for five days with X-irradiated (20,000 rads) EG7-OVA cells ($15 \times 10^6$ cells), in 10 ml of media. EG7 is a EL4 tumor cell line transfected with OVA cDNA)(Moore et al, Cell, 54:777 (1988)).

After five days of culture, the cells were tested for their ability to lyse $^{51}$Cr-labeled EL4 cells (C57BL/6, H$2^b$ thymoma) or EG7 cells, in accordance with conventional techniques.

The results of the experiment are illustrated in FIGS. 6A–6D. As shown, the particulate OVA antigen complexes primed CTL response at 90 and 18 $\mu$g (FIGS. 6A and 6B, respectively); the same amount of soluble OVA was ineffective (FIGS. 6C and 6D, respectively) to elicit a CTL response.
Experiment B.

Figure 7A:
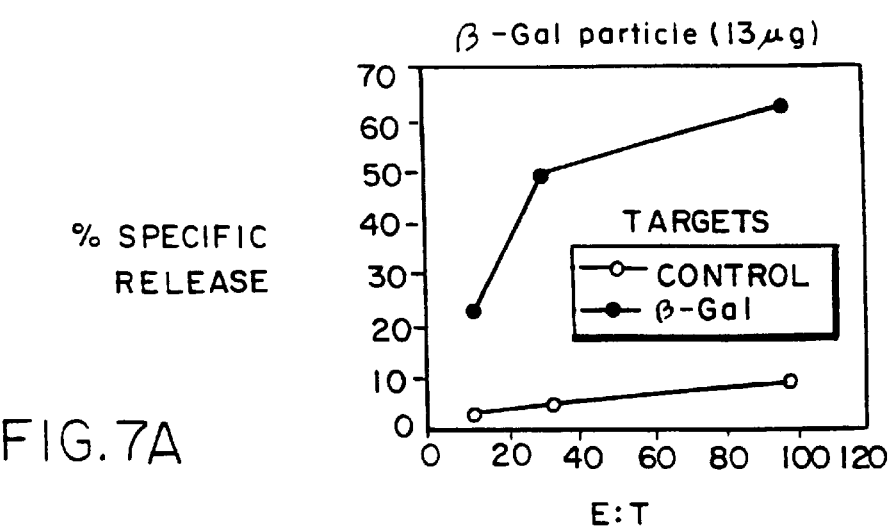
FIG. 7A through FIG. 7C depicts the results of a chromium release assay which demonstrates the ability of particulate protein antigen complexes to prime CTL responses in vivo. C57BL/6 mice were injected subcutaneously with the indicated antigen preparations (β-gal=E. coli β-galactosidase linked to iron oxide particles), with the amount of antigen indicated at the top of the Figures. Seven days later, the animals were sacrificed and splenocytes restimulated in vitro with irradiated P13.4 cells. After five days of culture, the cells were tested for their ability to lyse 51Cr-labeled P815 or P13.4 cells. The percent specific release of chromium was measured for the indicated effector to target ratios (E:T).
Figure 7B:
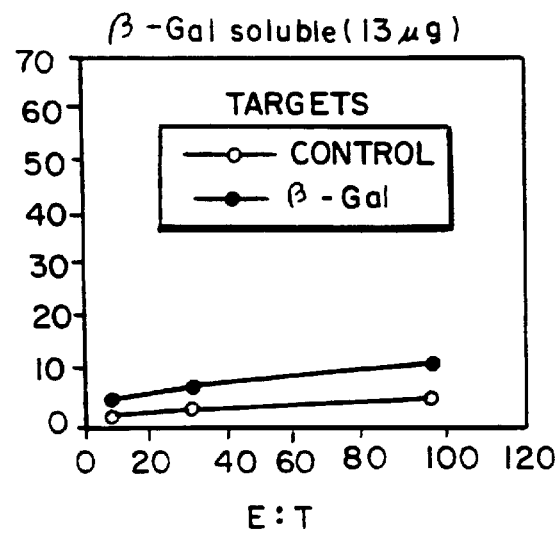
Figure 7C:
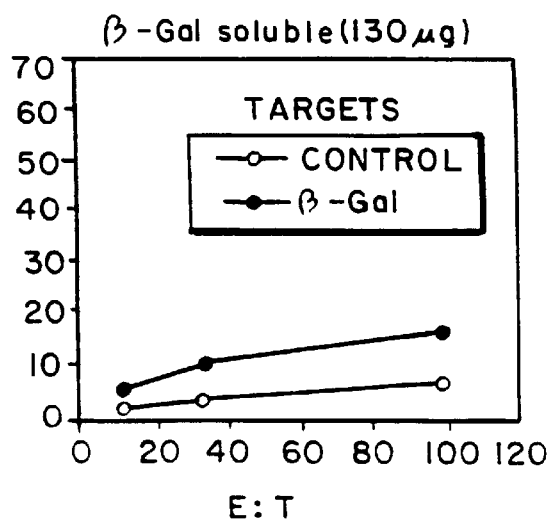

This experiment was similar to the one described in paragraph A immediately above, except that the antigen used was native E. coli β-galactosidase (β-gal) (mw approximately 540 kd), instead of chicken OVA. β-gal-iron oxide particles were prepared as described in Example 2A, formulated with phosphate buffered saline (PBS) and separately injected subcutaneously into both flanks of Balb/c mice. The amount of antigen injected was either 13 $\mu$g or 130 $\mu$g, as indicated in FIGS. 7A through 7C. Five weeks following the injections, the mice were sacrificed and their spleen cells removed. Spleen cells ($35 \times 10^6$ were restimulated in vitro for five days with $3 \times 10^6$ X-irradiated (20,000 rads) P13.4 cells. P13.4 is a mastocytoma cell line transfected with β-gal cDNA, that was generated in accordance with established recombinant DNA techniques.

After five days of culture, the cells were tested for their ability to lyse $^{51}$Cr-labeled P815 cells (DBA/2, H$2^d$ mastocytoma) or P13.4 cells, in accordance with conventional techniques.

The results of the experiment are illustrated in FIGS. 7A–7C. As shown, the particulate β-gal antigen complexes primed CTL response at 13 $\mu$g (FIG. 7A), while the same amount of soluble β-gal (FIG. 7B), and ten times the amount of β-gal (FIG. 7C), were not effective.
Experiment C.

This Experiment was similar to the ones described in the preceding paragraphs, except that the antigen used was native hen egg lysozyme ("HEL") (mw approximately 15 kd). HEL-iron oxide particles were prepared as described in Example 2A, formulated with phosphate buffered saline and (PBS) injected subcutaneously into both flanks of C57Bl/6 mice. Three weeks following the injections, the mice were sacrificed and their spleen cells removed. Spleen cells ($5 \times 10^6$) were restimulated in vitro overnight with $5 \times 10^6$ X-irradiated (20,000 rads) a CNBr-cleaved peptide preparation of HEL (100–300 $\mu$g/ml), in 1 ml media with rat con A SN/alpha methyl mannoside (05. %).

After five days of culture, the cells were tested for their ability to lyse $^{51}$Cr-labeled EL4 cells in the presence of CNBr-cleaved peptides of HEL or EL4 cells, in accordance with conventional techniques.

Figure 8A:
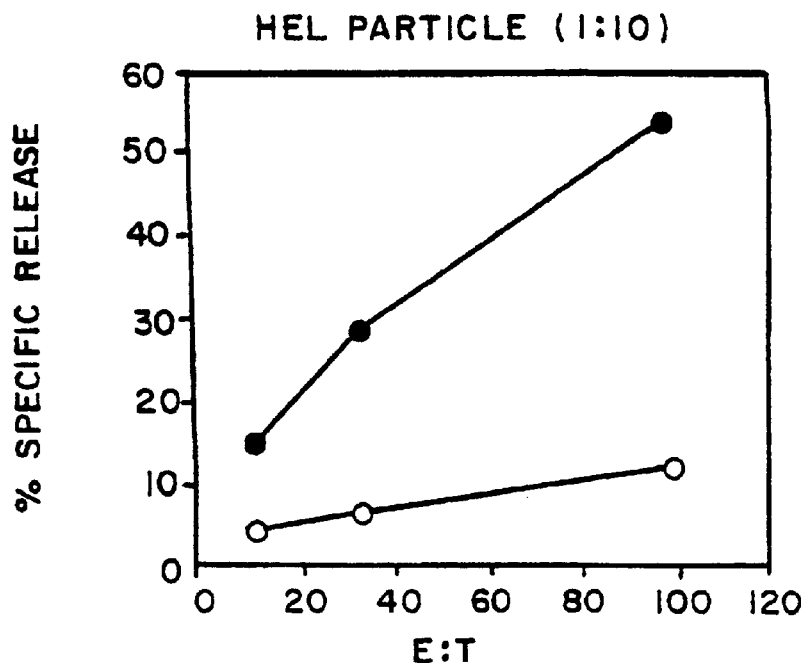
FIG. 8A and FIG. 8B show that the protein hen enzyme lysozyme (HEL), can prime CTL's in mice in vivo, when linked to an iron oxide particle in accordance with the present invention.
Figure 8B:
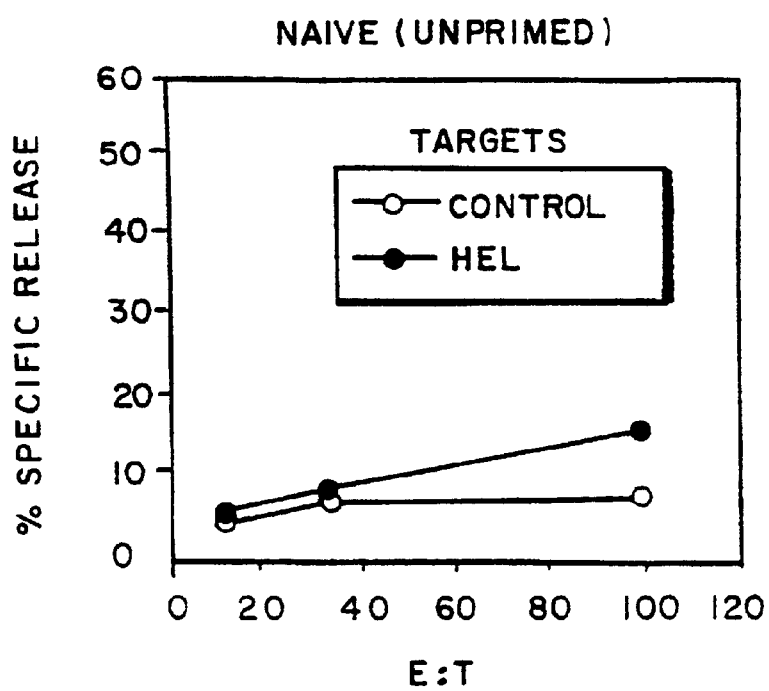

The results of the experiment are illustrated in FIGS. 8A and 8B. As shown in the Figure, the particulate HEL antigen complexes primed CTL response (FIG. 8A), while the naive (unprimed) animals did not respond under the same conditions.

The results of the foregoing experiments, which were conducted with unrelated antigens, establish a general pathway for uptake, processing, and presentation of antigen by a subpopulation of antigen presenting cells.

EXAMPLE 5

This Example describes the induction of a CTL response to an HIV antigen in mice in vivo using a particulate antigen complex of the invention.

Soluble recombinant HIV-1-IIIB gp160 envelope glycoprotein is prepared from cells infected with a recombinant baculovirus expressing the gene for gp160 of HIV-1-IIIB, as previously described. Javaherian et al., Proc. Natl. Acad. Sci. USA, 86:6768 (1989). The protein can be purified as also described by Javaherian et al. The purified product is a single band on SDS-PAGE, as seen by both Coomassie blue staining and by Western blotting with a monoclonal anti-gp41 antibody.

The purified HIV-1 gp160 envelope protein is then linked to POLYBEAD Amino Microspheres (Polysciences, Inc) (1 $\mu$m average diameter) using glutaraldehyde to activate the particles, in accordance with the manufacturer's instructions. The particulate antigen complex is formulated with a pharmaceutically acceptable excipient, such as phosphate buffered saline and injected subcutaneously into both flanks of BALB/c mice, which can be purchased from Jackson Laboratory, Bar Harbor, Me. The amount of the particulate/recombinant HIV-160 gp glycoprotein complex is 10 μg. In a separate experiment, a pair of age and sex matched BALB/c mice are injected with soluble recombinant HIV-1 gp 160 glycoprotein (10 μg).

Approximately seven days following the injections, the mice are sacrificed and their spleen cells removed. To test for CTL activity, spleen cells ($5 \times 10^6$) are restimulated in vitro for five days with mitomycin C treated ($50 \mu g/ml^{-1}$, 45 min., 37° C.) BALB/c3T3 fibroblasts that are transfected to express the whole gp160IIIB envelope protein, in complete T cell medium.

After six days of culture, the cells are tested for their ability to lyse $^{51}$Cr-labeled BALB/c3T3 transfectants expressing the whole gp160IIIB envelope protein or nongp160IIIB expressing BALB/c3T3 cells pulsed with 1 μm peptide 18IIB, which is a 15 residue synthetic peptide corresponding to an immunodominant CTL epitope of HIV-1 gp 160. Takahashi, *Proc. Natl. Acad. Sci.*, 85:3105–3109 (1988).

CTL's from mice immunized with the gp 160 glycoprotein-POLYBEAD complex are obtained that specifically lyse fibroblast targets either expressing gp160IIIB envelope protein or pulsed with the 15 residue 18IIIB peptide. In contrast, similarly restimulated spleen cells from mice immunized with soluble protein alone should fail to efficiently elicit a CTL response to either of these targets. This experiment suggests that it may be possible to elicit human CTL by using particulate antigen complexes of HIV antigens.

EXAMPLE 6

This Example demonstrates, using an accepted animal model of tumor immunity, that the particulate protein antigen complexes of the invention can be used to induce tumor immunity.
Experiment A OVA-iron oxide particles and soluble OVA were prepared as described in Example 2A, formulated with phosphate buffered saline (PBS), and separately injected subcutaneously into both flanks of C57Bl/6 mice (five per group), purchased from the Jackson Laboratory, Bar Harbor, Me., or bred at the Dana-Farber Cancer Institute (Boston, Mass.). The amount of protein antigen complex injected was 75 μg. A second group of mice was immunized with the same amount of soluble ovalbumin in saline, while a third group was not immunized. Ten days following the immunizations, the mice were challenged subcutaneously with $1 \times 10^5$ MO4 cells, which are syngeneic B16 melanoma cells that have been transfected with cDNA encoding chicken ovalbumin and tumor growth was monitored every two days commencing on day six after challenge.

Figure 9:
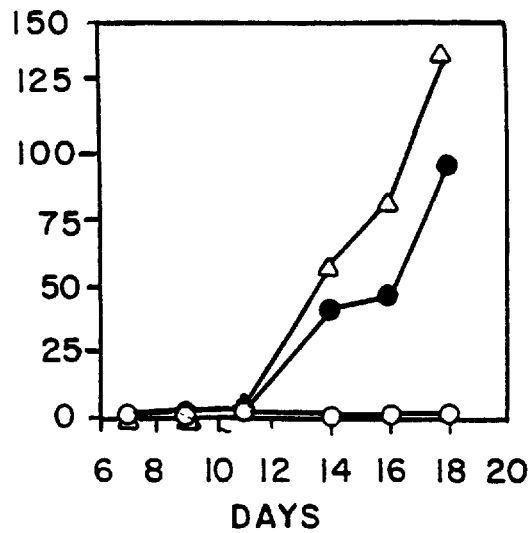
FIG. 9 depicts the results of a tumor growth assay which demonstrates in a model of tumor immunity that immunization with ovalbumin conjugated to iron oxide particles inhibits tumor formation in mice subsequently challenged with B16 melanoma cells transfected with a cDNA encoding chicken ovalbumin. In the Figure, the open circles represent the mice immunized with ovalbumin conjugated to the iron oxide, the closed circles represent the mice immunized with ovalbumin alone, and the open triangles represent the mice that were unimmunized.

The resulting data are illustrated in FIG. 9. As illustrated in this figure, the mice that had been immunized with the OVA-iron oxide beads (open circles) showed virtually no tumor volume, while those that had not been immunized (open triangles), and those that had been immunized with the soluble OVA (closed circles) began to show significant increase in tumor volume on about day 12, with continued increase in tumor volume over the next several days.
Experiment B OVA-iron oxide particles and soluble OVA were again prepared as described in Example 2A, formulated with phosphate buffered saline (PBS), and separately injected subcutaneously into both flanks of C57Bl/6 mice (ten per group), purchased from the Jackson Laboratory, Bar Harbor, Me, or bred at the Dana-Farber Cancer Institute (Boston, Mass.). The amount of protein antigen complex injected was 50 μg in saline. A second group of mice was not immunized. Seven days following the immunizations, the mice were challenged subcutaneously with $1 \times 10^7$ EG7 cells, which are syngeneic EL4 lymphoma cells that have been transfected with cDNA encoding chicken ovalbumin. Survival of the challenged mice was monitored over a period of 140 days commencing immediately after challenge.

Figure 10:
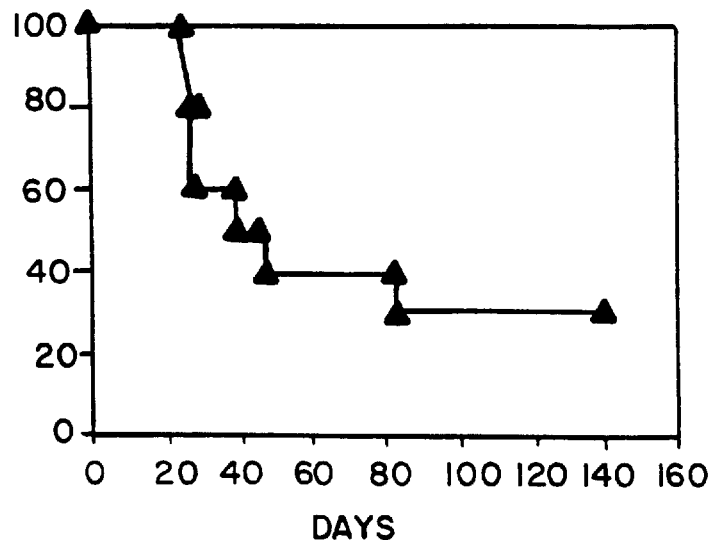
FIG. 10 depicts the results of a survival assay which demonstrates in a model of tumor immunity that immunization with ovalbumin conjugated to iron oxide particles significantly increases survival of mice subsequently challenged with EL4 lymphoma cells transfected with a cDNA encoding chicken ovalbumin compared to animals that had not been immunized. In the Figure, the open triangles represent the mice immunized with ovalbumin conjugated to the iron oxide and the closed triangles represent mice that were not immunized.

The data from this Experiment are set forth in FIG. 10. As illustrated in this figure, the mice that had been immunized with the OVA-iron oxide beads (open triangles) showed 100% survival at 140 days post-challenge, while those that had not been immunized showed only about 35% survival on day 140.

EXAMPLE 7

This Example demonstrates that a particulate-influenza complex in accordance with the invention can confer protective immunity in a mammal from subsequent challenge with live influenza virus.

In this Example, a commercially available, formaldehyde-inactivated influenza virus vaccine was covalently coupled to BIOMAG (TM) magnetized iron oxide particles, which are coated to provide amino groups. The complexes were prepared substantially as described in Example 2A, except that the antigen used was the Influenza Virus Vaccine, Trivalent, Type A (Wyeth Laboratories, Inc., Marietta, Pa.) instead of chicken ovalbumin. The complexes were formulated with phosphate buffered saline (PBS), and separately injected subcutaneously into both flanks of Balb/C mice (five per group), purchased from the Jackson Laboratory, Bar Harbor, Me., or bred at the Dana-Farber Cancer Institute (Boston, Mass.). The amount of protein antigen complex injected was 50 μg in saline. A second group of mice was not immunized. Seven days following the immunizations, the mice were challenged intranasally with live influenza virus (strain A/MEL/35, dose=4X LD50). Survival of the challenged mice was monitored over a period of 12 days commencing immediately after challenge.

Figure 11:
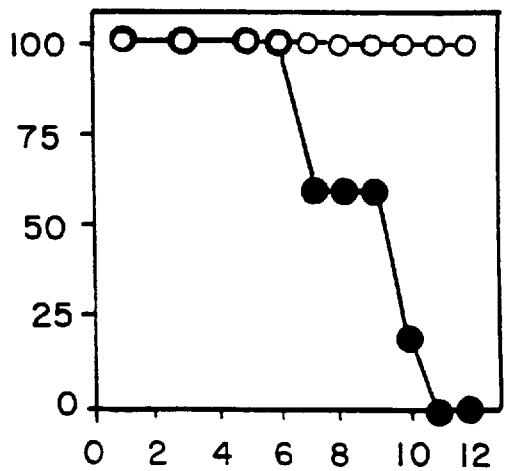
FIG. 11 depicts the results of a survival assay which demonstrates that immunization with a commercially-available inactivated influenza virus preparation conjugated to iron oxide particles significantly increased survival of mice subsequently challenged intranasally with the inactivated virus compared to animals that had not been immunized. In the Figure, the open circles represent the mice immunized with inactivated influenza virus strain A conjugated to the iron oxide and the closed circles represent mice that were not immunized.

The data from this Experiment are illustrated in FIG. 11. As illustrated in this figure, the mice that had been immunized with the inactivated influenza-iron oxide beads (open circles) showed 100% survival at 12 days post-challenge, while those that had not been immunized had all died as of day 12.

EXAMPLE 8

This Example indicates that CD4+ T cells are not necessary for effectiveness of the immunogens of the invention, and also that the complexes of the invention can be used to prime a CTL response in immunodeficient animals.

In this experiment, C57Bl/6 or class II MHC-deficient mutant mice were immunized subcutaneously in both flanks with ovalbumin conjugated to iron oxide particles (25 μg) prepared as described in Example 2A. The class II mutant mice are animals which are lacking in class II molecules due to the disruption of $IA^b$ through homologous recombination. See, Gusby, M. J., "Development of CD4+ T Cells In MHC Class II-Deficient Mice'" *Science*, 253:1417–1420 (1991). These mice express no class II molecules and hence fail to develop CD4+ T lymphocytes. Id. The mice can be generated as described in Grusby et al, and are also available commercially from GenPharm International, (Mountain View, Calif.).

Seven days after immunization, one group of animals was reimmunized with the same immunogen. Fourteen days after the initial immunization, all animals were sacrificed, spleen cells removed, and restimulated in vitro with irradiated with EG7 cells. More specifically, spleen cells ($30 \times 10^6$) were restimulated in vitro for five days with X-irradiated (20,000 rads) EG7-OVA cells ($15 \times 10^6$ cells), in 10 ml of media. EG7 is a EL4 tumor cell line transfected with OVA cDNA) (Moore et al, *Cell*, 54:777 (1988)).

After five days of culture, the cells were tested for their ability to lyse $^{51}$Cr-labeled EL4 cells (BG) (C57BL/6, H2$^b$ thymoma) or EG7 cells, in accordance with conventional techniques.

Figure 12A:
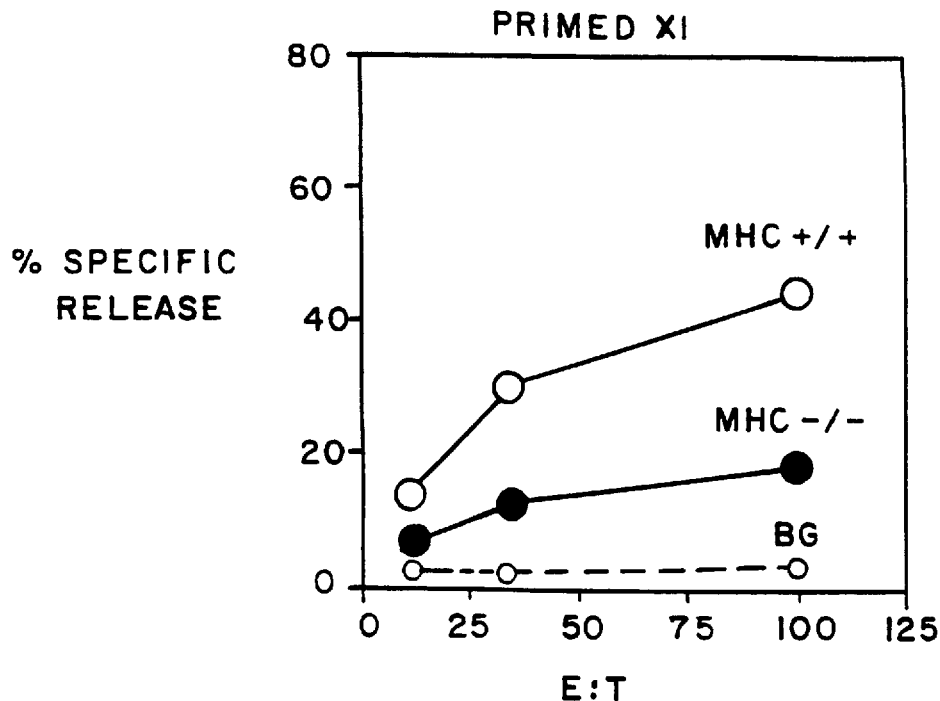
FIGS. 12A and 12B depict the results of a chromium release assay which demonstrates the ability of particulate protein antigen complexes to prime CTL responses in vivo in immunodeficient mice. C57BL/6 or MHC class II mutant mice were injected subcutaneously with ovalbumin conjugated to iron oxide beads (25 μg) Seven days later, one group of the mice was reimmunized with the same immunogen. Fourteen days after the initial immunization the animals were sacrificed and splenocytes restimulated in vitro with irradiated EG7 cells. After five days of culture, the cells were tested for their ability to lyse $^{51}$Cr-labeled EL4 cells (BG) or EG7 cells. The percent specific release of chromium was measured for the indicated effector to target ratios (E:T).
Figure 12B:
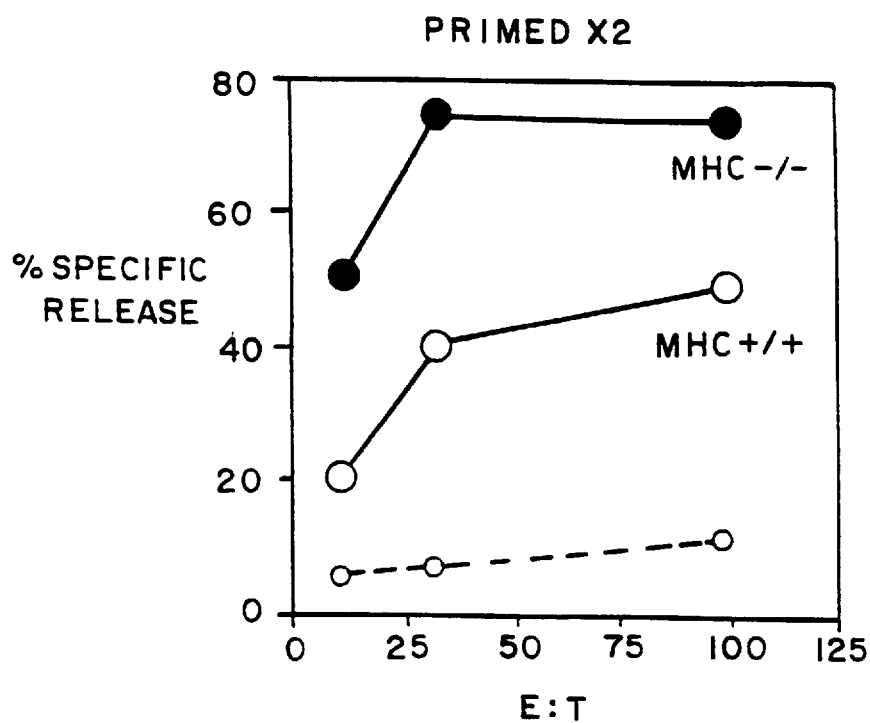

The results of the experiment are illustrated in FIGS. 12A and 12B. As shown in these figures, the particulate OVA antigen complexes primed CTL's in both the normal C57Bl/6 mice (MHC+/+) and the immunodeficient mutant mice (MHC −/−). Immunodeficient mice that had been immunized twice (FIG. 12B, Primed×2) showed greater response than did the immunodeficient mice that had been primed only once (FIG. 12A, Primed×1).

These data indicate that use of the particulate protein antigen complexes of the invention in vivo is a strong form of immunization.

I claim:

1. A method for inducing a class I-restricted CTL response to a protein antigen in a mammal, comprising administering to a mammal a pharmaceutical composition comprising a pharmaceutically acceptable excipient and a particulate-protein complex
   wherein the particulate protein complex comprises a particulate component having an average diameter ranging in size from about 0.5 µm to about 6 µm and having an outer surface linked to a non-replicating protein antigen derived from a pathogenic organism, with the proviso that the particulate component is not a prokaryotic or eukaryotic cell, a micellar, multimicellar, or liposome vesicle, or composed of detergents or lipids;
   wherein the protein antigen is taken up, processed and presented in association with MHC class I molecules by an antigen presenting cell; and
   wherein the particulate-protein complex is administered in an amount effective to induce a class I-restricted CTL response to the protein antigen in the mammal.

2. A method according to claim 1, wherein the non-replicating protein antigen is linked to the particle component through a covalent linkage.

3. A method according to claim 1, wherein the non-replicating protein antigen is linked to the particle component through a non-covalent linkage.

4. A method according to claim 1, wherein the non-replicating protein antigen is a viral protein.

5. A method according to claim 4, wherein the viral protein is derived from a virus selected from the group consisting of influenza viruses, retroviruses, POX viruses, Herpes viruses, respiratory syncytial viruses, rabies viruses, measles viruses, polio viruses and rotaviruses.

6. A method according to claim 1, wherein the non-replicating protein antigen is a bacterial protein.

7. A method according to claim 1, wherein the particulate component is an iron-oxide particle.

8. A method according to claim 1, wherein the particulate component is a silica bead.

9. A method according to claim 1, wherein the particulate component is a latex bead.

10. A method according to claim 1, wherein the particulate component is a biocompatible polymer or copolymer selected from the group consisting of polysaccharides, proteins and oligosaccharides formed of two or more monosaccharides linked by glycosidic bonds.

11. A method for inducing a class I-restricted CTL response to a protein antigen in a mammal, comprising administering to a mammal a pharmaceutical composition comprising a pharmaceutically acceptable excipient and a particulate-protein complex
    wherein the particulate protein complex comprises a particulate component having an average diameter ranging in size from about 0.5 µm to about 6 µm and having an outer surface linked to a tumor antigen, with the proviso that the particulate component is not a prokaryotic or eukaryotic cell, a micellar, multimicellar, or liposome vesicle, or composed of detergents or lipids;
    wherein the antigen is taken up, processed and presented in association with MHC class I molecules by an antigen presenting cell; and
    wherein the particulate-protein complex is administered in an amount effective to induce a class I-restricted CTL response to the antigen in the mammal.

12. A method according to claim 11, wherein the non-replicating protein antigen is linked to the particle component through a covalent linkage.

13. A method according to claim 11, wherein the non-replicating protein antigen is linked to the particle component through a non-covalent linkage.

14. A method according to claim 11, wherein the particulate component is an iron-oxide particle.

15. A method according to claim 11, wherein the particulate component is a silica bead.

16. A method according to claim 11, wherein the particulate component is a latex bead.

17. A method according to claim 11, wherein the particulate component is a biocompatible polymer or copolymer selected from the group consisting of polysaccharides, proteins and oligosaccharides formed of two or more monosaccharides linked by glycosidic bonds.

18. A method for inducing a class I-restricted CTL response to a protein antigen in a mammal, comprising administering to a mammal a pharmaceutical composition comprising a pharmaceutically acceptable excipient and a particulate-protein complex
    wherein the particulate protein complex comprises a particulate component having an average diameter of about 10 µm and having an outer surface linked to a non-replicating protein antigen derived from a pathogenic organism, with the proviso that the particulate component is not a prokaryotic or eukaryotic cell, a micellar, multimicellar, or liposome vesicle, or composed of detergents or lipids;
    wherein the protein antigen is taken up, processed and presented in association with MHC class I molecules by an antigen presenting cell; and
    wherein the particulate-protein complex is administered in an amount effective to induce a class I-restricted CTL response to the protein antigen in the mammal.

19. A method for inducing a class I-restricted CTL response to a bacterial protein antigen in a mammal, comprising administering to a mammal a pharmaceutical composition comprising a pharmaceutically acceptable excipient and a particulate-protein complex
    wherein the particulate protein complex comprises a particulate component having an average diameter ranging in size from about 0.5 μm to about 6 μm and having an outer surface linked to a bacterial protein antigen, with the proviso that the particulate component is not a prokaryotic or eukaryotic cell, a micellar, multimicellar, or liposome vesicle, or composed of detergents or lipids;

wherein the protein antigen is taken up, processed and presented in association with MHC class I molecules by an antigen presenting cell; and wherein the particulate-protein complex is administered in an amount effective to induce a class I-restricted CTL response to the protein antigen in the mammal.

20. A method for inducing a class I-restricted CTL response to a viral protein antigen in a mammal, comprising administering to a mammal a pharmaceutical composition comprising a pharmaceutically acceptable excipient and particulate-protein complex wherein the particulate protein complex comprises a particulate component having an average diameter ranging in size from about 0.5 μm to about 6 μm and having an outer surface linked to a viral protein antigen, with the proviso that the particulate component is not a prokaryotic or eukaryotic cell, a micellar, multimicellar, or liposome vesicle, or composed of detergents or lipids;

wherein the protein antigen is taken up, processed and presented in association with MHC class I molecules by an antigen presenting cell; and wherein the particulate-protein complex is administered in an amount effective to induce a class I-restricted CTL response to the protein antigen in the mammal.

* * * * *